(12) United States Patent
Takayama et al.

(10) Patent No.: US 8,373,528 B2
(45) Date of Patent: Feb. 12, 2013

(54) MAGNETIC FIELD CONTROL METHOD AND MAGNETIC FIELD GENERATOR

(75) Inventors: Yoshinori Takayama, Osaka (JP); Mitsutoshi Natsumeda, Nara (JP); Kentaro Horisaka, Nagoya (JP)

(73) Assignee: Hitachi Metals, Ltd., Tokyo (JP)

( * ) Notice: Subject to any disclaimer, the term of this patent is extended or adjusted under 35 U.S.C. 154(b) by 1129 days.

(21) Appl. No.: 12/296,589

(22) PCT Filed: Jul. 13, 2007

(86) PCT No.: PCT/JP2007/063977
§ 371 (c)(1),
(2), (4) Date: Oct. 9, 2008

(87) PCT Pub. No.: WO2008/007771
PCT Pub. Date: Jan. 17, 2008

(65) Prior Publication Data
US 2009/0076324 A1 Mar. 19, 2009

(30) Foreign Application Priority Data
Jul. 13, 2006 (JP) .................................. 2006-192503

(51) Int. Cl.
*H01F 1/00* (2006.01)
*H01F 3/00* (2006.01)
*H01F 7/00* (2006.01)
*A61B 5/05* (2006.01)
(52) U.S. Cl. ........ 335/296; 335/284; 335/298; 335/302; 335/304; 335/306; 600/117; 600/424
(58) Field of Classification Search .................. 335/219, 335/284, 296, 298, 302, 304, 306; 600/117, 600/424
See application file for complete search history.

(56) References Cited

U.S. PATENT DOCUMENTS 5,681,260 A 10/1997 Ueda
6,011,396 A * 1/2000 Eckels et al. .................. 324/319
(Continued)

FOREIGN PATENT DOCUMENTS

EP 1547540 A1 6/2005
EP 1 929 943 A1 6/2008
(Continued)

OTHER PUBLICATIONS

European Search Report dated Jul. 6, 2010 for corresponding to EPC Patent Application No. 07790758.2.
(Continued)

*Primary Examiner* — Mohamad Musleh
(74) *Attorney, Agent, or Firm* — Kratz, Quintos & Hanson, LLP

(57) ABSTRACT

There is provided a magnetic field control method and a magnetic field generator which are capable of moving a local maximum point of magnetic field intensity on a predetermined plane easily to any given point within a predetermined area on the predetermined plane. A magnetic field generator 10 includes a pair of permanent magnets 16a, 16b provided axially of a predetermined axis A, with a gap G in between. The permanent magnet 16a is formed on a drive unit 14a in such a way that a center region 30a of a first main surface 26a is off the predetermined axis A. The permanent magnet 16b is formed on a drive unit 14b in such a way that a center region 30b of a first main surface 26b is off the predetermined axis A. The permanent magnet 16a revolves on a path R1 as a rotating member 24a rotates. The permanent magnet 16b revolves on a path R2 as a rotating member 24b rotates. A local maximum point M is moved on an X-Y plane by performing at least one of a first operation of revolving the permanent magnets 16a, 16b relatively to each other and a second operation of revolving the permanent magnets 16a, 16b in the same direction by the same angle.

9 Claims, 19 Drawing Sheets

U.S. PATENT DOCUMENTS

| | | |
|---|---|---|
| 6,185,448 B1 | 2/2001 | Borovsky ............... 600/424 |
| 7,479,859 B2 * | 1/2009 | Gerber ................. 335/296 |
| 7,706,858 B1 * | 4/2010 | Green et al. ........... 600/415 |
| 2004/0249262 A1 | 12/2004 | Werp |
| 2004/0249263 A1 | 12/2004 | Creighton, IV ......... 600/411 |
| 2005/0113628 A1 | 5/2005 | Creighton, IV et al. ..... 600/1 |
| 2005/0187424 A1 | 8/2005 | Hambuchen |
| 2009/0231073 A1 * | 9/2009 | Horisaka et al. ........ 335/209 |

FOREIGN PATENT DOCUMENTS

| | | |
|---|---|---|
| JP | 55-133237 | 10/1980 |
| JP | 4-8343 | 1/1992 |
| JP | 2000-229844 | 8/2000 |
| JP | 2002-538885 | 11/2002 |
| JP | 2005-103091 A1 | 4/2005 |
| JP | 2005-161052 A1 | 6/2005 |
| JP | 2008-503310 | 2/2008 |
| WO | WO 00/54690 | 9/2000 |
| WO | WO 03/083880 A1 | 10/2003 |
| WO | WO 2005/122866 A1 | 12/2005 |
| WO | WO 2007/037380 A1 | 4/2007 |

OTHER PUBLICATIONS

International Search Report for International Application No. PCT/JP2007/063977 dated Jul. 27, 2007.

PCT Notification of Transmittal of Translation of the International Preliminary Report on Patentability (PCT Chapter I) dated Jan. 29, 2009.

Decision to Grant a Patent of the corresponding JP application No. 2008-524854 dated Apr. 24, 2012.

* cited by examiner

F I G. 1 0
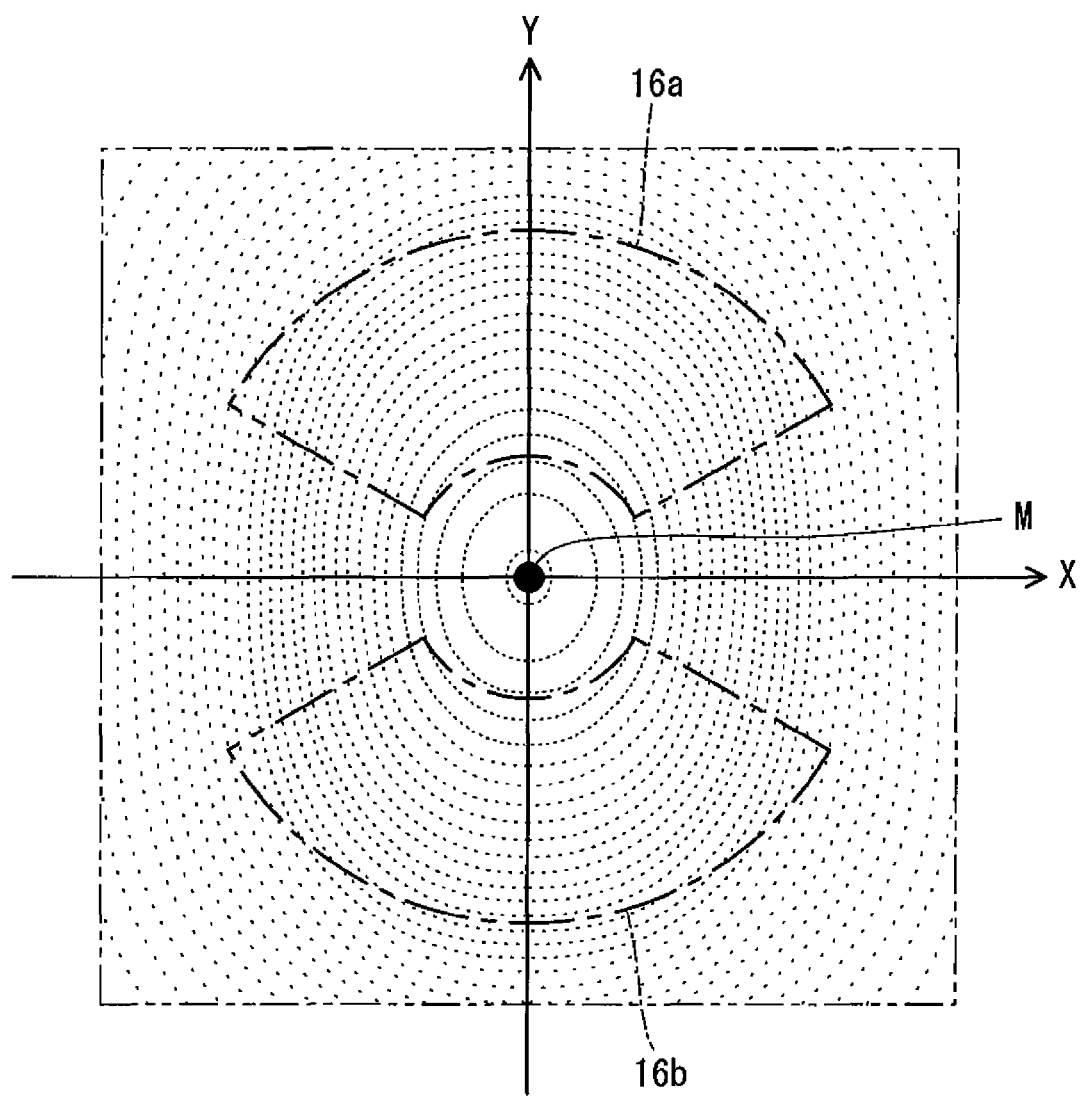

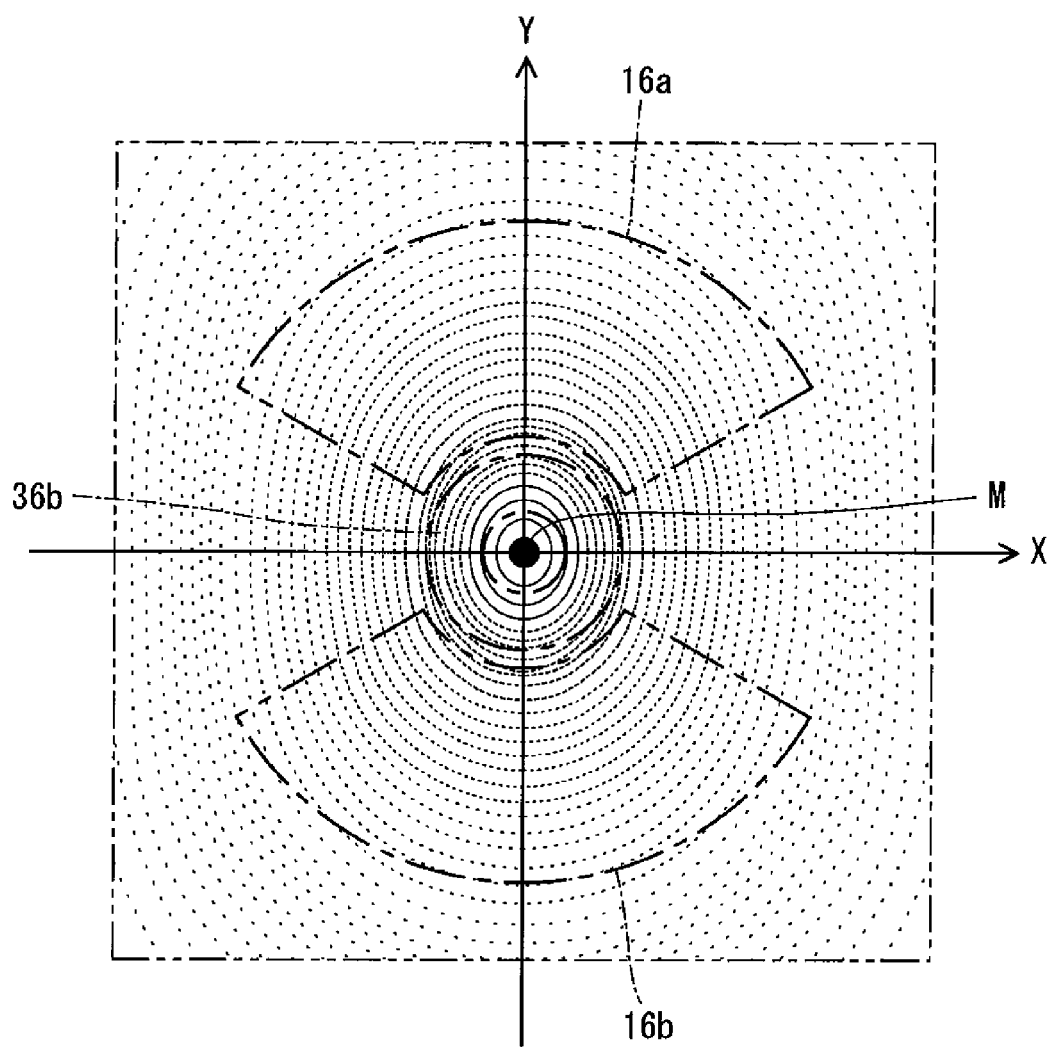
F I G. 1 4

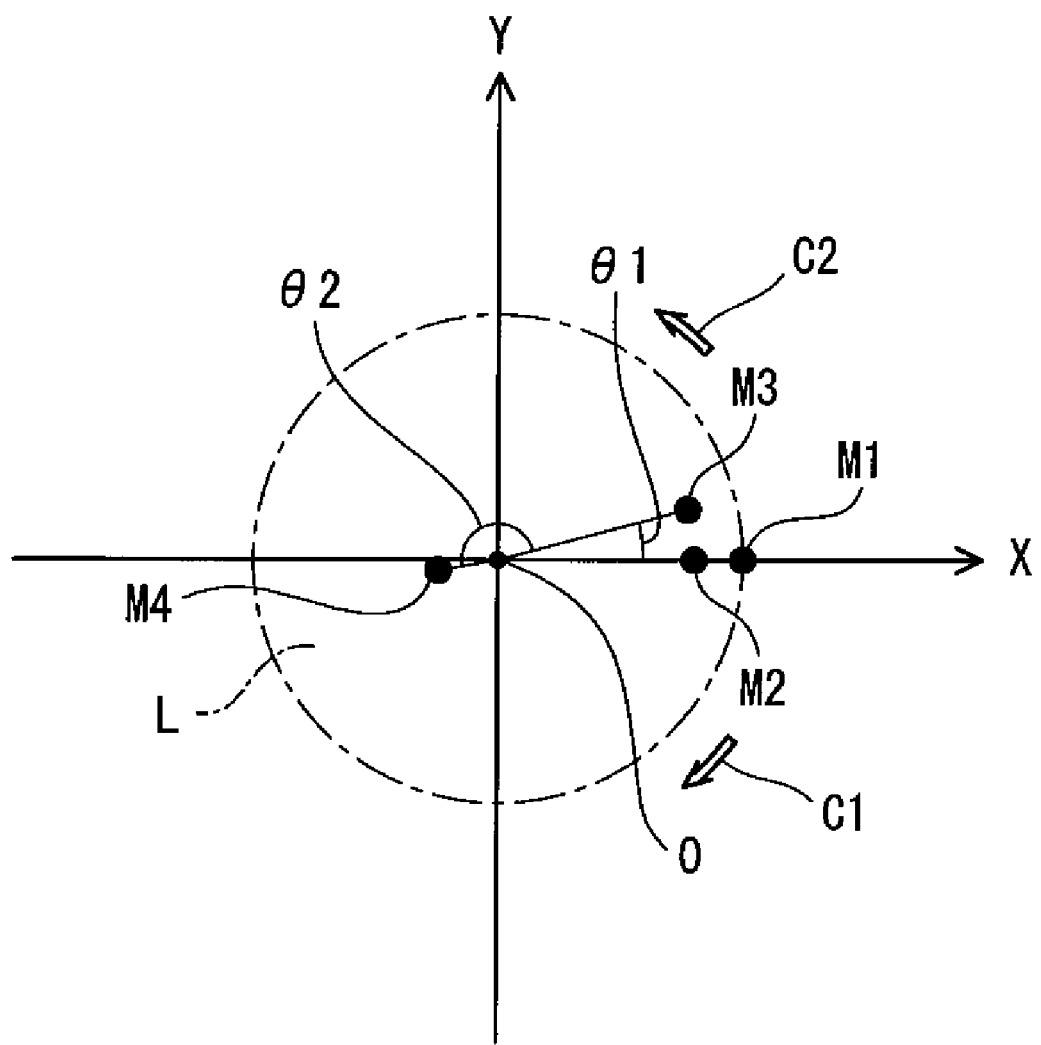
F I G. 1 8

FIG. 19
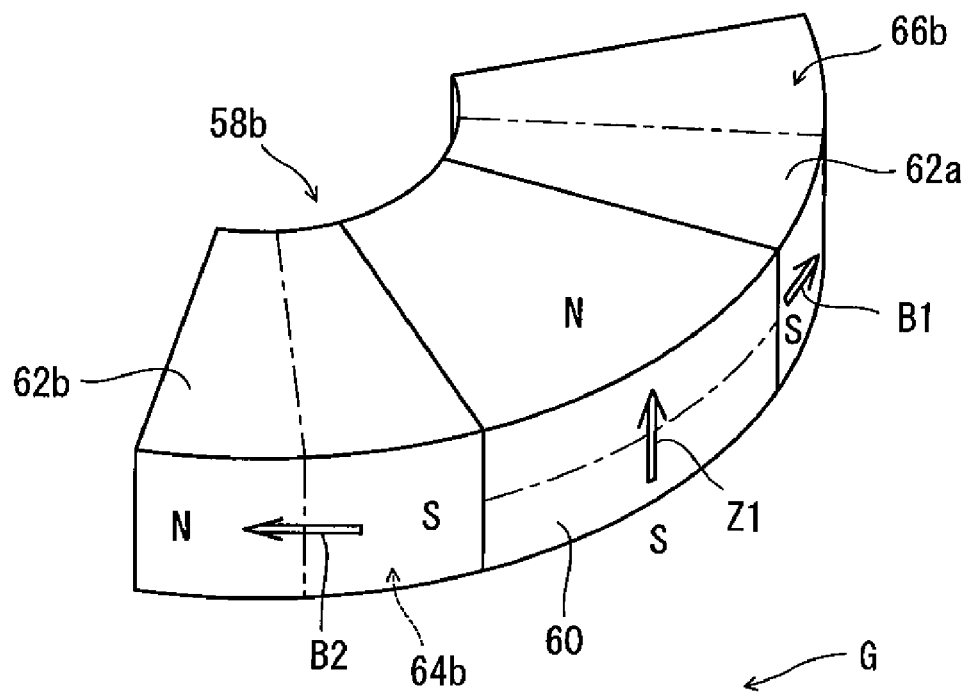
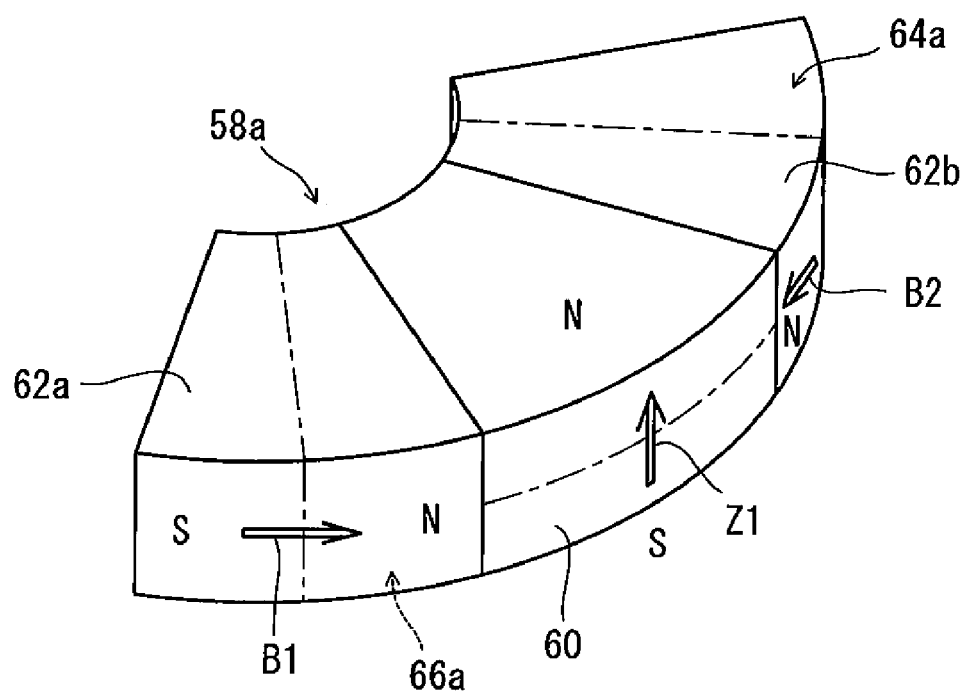

MAGNETIC FIELD CONTROL METHOD AND MAGNETIC FIELD GENERATOR

TECHNICAL FIELD

The present invention relates to a magnetic field control method and a magnetic field generator, and more specifically to a magnetic field control method and a magnetic field generator whereby a local maximum point of magnetic field intensity on a predetermined plane can be moved.

BACKGROUND ART

In recent years, attention has been paid in the field of medical care to medical instrument guide systems which guide medical instruments such as a capsule endoscope and a catheter to a target position inside the body, and to drug delivery systems which delivers a drug to a target position inside the body. As such guide systems, Patent Documents 1 and 2 disclose magnetic guide systems which guide an object that contains magnetic material to a target position inside the body by work of a magnetic field generated by a magnetic field generator.

In the magnetic field generators disclosed in Patent Documents 1 and 2, a pair of magnetic field generation units connected by a connecting member is moved with a supporting member, whereby a magnetic field generated by the pair of magnetic field generation units is moved and a local maximum point of magnetic field intensity on a predetermined plane is moved. The object which contains magnetic material is drawn to the local maximum point of magnetic field intensity, so it is possible to move the object by moving the local maximum point of magnetic field intensity.

Patent Document 1: JP-A Hei 4-8343
Patent Document 2: JP-A 2005-103091

DISCLOSURE OF THE INVENTION

Problems to be Solved by the Invention

However, according to the techniques disclosed in Patent Documents 1 and 2, it is necessary to move, together with the pair of magnetic field generation units, the connecting member which connects the pair of magnetic field generation units with each other, the support member which supports the pair of magnetic field generation units and the connecting member and so on. This poses a problem that the apparatus has a complicated configuration. Particularly, in order to move the local maximum point to any given position within a predetermined area on a predetermined plane, it is necessary, as described in Patent Document 1, to move the pair of magnetic field generation units in two directions, and this makes configuration and control of the apparatus more complicated.

Therefore, a primary object of the present invention is to provide a magnetic field control method and a magnetic field generator capable of moving the local maximum point of magnetic field intensity on a predetermined plane easily to any given position within a predetermined area on the predetermined plane.

Means for Solving the Problems

According to an aspect of the present invention, there is provided a magnetic field control method of controlling a magnetic field generated by a pair of magnetic field generation units provided axially of a predetermined axis to face each other with a gap in between, each of the units having a gap-side main surface formed with a magnetic pole of an opposite polarity from each other, each magnetic pole being so disposed as to cause a magnetic flux density near the gap-side main surface to attain a local maximum off the predetermined axis, the magnetic field being controlled on a predetermined plane perpendicular to the predetermined axis and between the pair of magnetic field generation units: The control method includes a step of moving a local maximum point of magnetic field intensity on the predetermined plane by performing at least one of a first operation of revolving one of the magnetic field generation units about the predetermined axis relatively to the other of the magnetic field generation units, and a second operation of revolving the pair of magnetic field generation units about the predetermined axis in a same direction by a same angle.

According to another aspect of the present invention, there is provided a magnetic field generator which includes a pair of magnetic field generation units provided axially of a predetermined axis to face each other with a gap in between, each of the units having a gap-side main surface formed with a magnetic pole of an opposite polarity from each other, each magnetic pole being so disposed as to cause a magnetic flux density near the gap-side main surface to attain a local maximum off the predetermined axis; first driving means for revolving one of the magnetic field generation units about the predetermined axis relatively to the other of the magnetic field generation units; and second driving means for revolving the pair of magnetic field generation units about the predetermined axis in a same direction by a same angle.

According to the present invention, when the magnetic field generation units in the pair are revolved relatively to each other in the first operation so that the two units will come closer to each other (so that the two units will have an increased overlap with each other), a position on the predetermined plane sandwiched by regions where magnetic flux density near the gap-side main surfaces in the pair of magnetic field generation units attains a maximum moves away from an intersection made by the predetermined axis and the predetermined plane. Likewise, when the magnetic field generation units in the pair are revolved relatively to each other in the first operation so that the two units will move away from each other (so that the two units will have a decreased overlap with each other), the position on the predetermined plane sandwiched by regions where magnetic flux density near the gap-side main surfaces in the pair of magnetic field generation units attains a maximum comes closer to the intersection made by the predetermined axis and the predetermined plane. The position on the predetermined plane sandwiched by regions where magnetic flux density near the gap-side main surfaces in the pair of magnetic field generation units attains a maximum is a place on the predetermined plane passed by the greatest amount of magnetic flux, and is a position where there is a local maximum point of magnetic field intensity on the predetermined plane. Therefore, as the position on the predetermined plane sandwiched by regions where magnetic flux density near the gap-side main surfaces in the pair of magnetic field generation units attains a maximum moves away from the intersection made by the predetermined axis and the predetermined plane, the local maximum point of magnetic field intensity on the predetermined plane moves away from the intersection made by the predetermined axis and the predetermined plane. Likewise, as the position on the predetermined plane sandwiched by regions where magnetic flux density near the gap-side main surfaces in the pair of magnetic field generation units attains a maximum moves closer to the intersection made by the predetermined axis and the predetermined plane, the local maximum point of magnetic field intensity on the predetermined plane comes closer to the intersection made by the predetermined axis and the predetermined plane. In other words, it is possible to move the local maximum point of magnetic field intensity on the predetermined plane so as to change the distance from the local maximum point of magnetic field intensity on the predetermined plane to the intersection made by the predetermined axis and the predetermined plane, by the first operation in which the pair of magnetic field generation units are revolved relatively to each other. On the other hand, by the second operation in which each of the magnetic field generation units in the pair is revolved about the predetermined axis in the same direction by the same angle, it is possible to move the local maximum point of magnetic field intensity on the predetermined plane while keeping the distance from the intersection made by the predetermined axis and the predetermined plane to the local maximum point of magnetic field intensity on the predetermined plane. By performing at least one of the first operation and the second operation as described, it is possible to move the local maximum point of magnetic field intensity on the predetermined plane to any given position within a predetermined area on the predetermined plane easily without need for the magnetic field generation units to perform a plurality of operations. According to the magnetic field generator offered by the present invention, it is possible to move the local maximum point easily to any given position within a predetermined area of a predetermined plane, by only a single operation of revolving the pair of magnetic field generation units. This makes possible to simplify the configuration.

Preferably, the magnetic field control method further includes a step of moving the predetermined plane in one direction along the axis by moving each of the magnetic field generation units in the pair in one direction by a same distance along the axis. In this case, it is possible to move the predetermined plane in one of the axial directions of the predetermined axis. Therefore, by combining the revolution of the pair of magnetic field generation units and the axial movement of the pair of magnetic field generation units along the predetermined axis, it becomes possible to move the local maximum point of magnetic field intensity on the predetermined plane to any position within a predetermined space. Such an axial movement of the pair of magnetic field generation units is performed by third driving means for example.

Also, it is preferable that the magnetic field generation unit includes a permanent magnet, and the magnetic pole on the gap-side main surface is formed on the permanent magnet. In this case, the permanent magnet is used as a source of magnetic field generation in the magnetic field generation unit. This makes possible to simplify constitution of the magnetic field generation unit, and to simplify configuration of the magnetic field generator. Further, since no energy supply is required to generate the magnetic field, it is possible to lower running cost.

Further, it is preferable that the permanent magnet included in the magnetic field generation unit does not reach the predetermined axis. In this case, it becomes possible to reduce the weight and manufacturing cost of the magnetic field generator by using a small permanent magnet which does not reach the predetermined axis. For example, a segment-shaped permanent magnet disposed on an annular locus is used.

When the pair of magnetic field generation units are revolved away from each other (so that the two units will have a decreased overlap with each other) in the first operation, the distance increases between the region where magnetic flux density near the gap-side main surface in one magnetic field generation unit of the pair attains a maximum and the region where magnetic flux density near the gap-side main surface in the other magnetic field generation unit of the pair attains a maximum. For this reason, the magnetic field gradient and the magnetic field intensity of the local maximum point on the predetermined plane decreases as the local maximum point comes closer to the intersection made by the predetermined axis and the predetermined plane in the case where none of the magnetic field generation units in the pair reaches the predetermined axis. Preferably, the magnetic field generation unit including the permanent magnet further includes an assisting permanent magnet disposed near the predetermined axis. In this case, the assisting permanent magnet provided near the predetermined axis gives a magnetic flux that is not smaller than a predetermined intensity to and around the intersection made by the predetermined axis and the predetermined plane. Therefore, it is possible to reduce magnetic field intensity drop in the local maximum point and magnetic field gradient drop on the predetermined plane even when the local maximum point comes to a vicinity of the intersection made by the predetermined axis and the predetermined plane.

Also, it is preferable that the permanent magnet included in the magnetic field generation unit reaches the predetermined axis. In this case, a portion of the permanent magnet reaching the predetermined axis gives a magnetic flux that is not smaller than a predetermined intensity to and around the intersection made by the predetermined axis and the predetermined plane. Therefore, it is possible to reduce magnetic field intensity drop in the local maximum point and magnetic field gradient drop on the predetermined plane even when the local maximum point comes to a vicinity of the intersection made by the predetermined axis and the predetermined plane. The permanent magnet may have a circular outer shape for example.

Further, it is preferable that the permanent magnet includes a first permanent magnet piece and a pair of second permanent magnet pieces opposed to each other with the first permanent magnet piece in between. With this arrangement, the magnetic pole on the gap-side main surface is formed on the first permanent magnet piece, and the second permanent magnet pieces have their mutually opposed surfaces being formed with magnetic poles of the same polarity as of the magnetic pole on the gap-side main surface. In this case, it is possible to draw more magnetic flux from the magnetic pole on the gap-side main surface if the pole is positive (N-pole). Likewise, it is possible to gather more magnetic flux to the magnetic pole on the gap-side main surface if the pole is negative (S-pole). Therefore, by using the permanent magnet of the above-described construction, it becomes possible to increase magnetic field gradient on the predetermined plane, and to increase magnetic field intensity at the local maximum point.

The above-described object, other objects, characteristics, aspects and advantages of the present invention will become clearer from the following detailed description of embodiments to be made with reference to the attached drawings.

BRIEF DESCRIPTION OF THE DRAWINGS

FIG. 10 is a diagram showing magnetic field intensity distribution on the X-Y plane under the state in FIG. 5.

FIG. 14 is a diagram showing magnetic field intensity distribution on the X-Y plane under the state in FIG. 13.

FIG. 18 is a diagram for describing a relationship between the position of local maximum point within a predetermined area and an angle by which a pair of permanent magnets are revolved.

FIG. 19 is a perspective diagram showing another example of the pair of magnetic field generation units.

Figure 1:
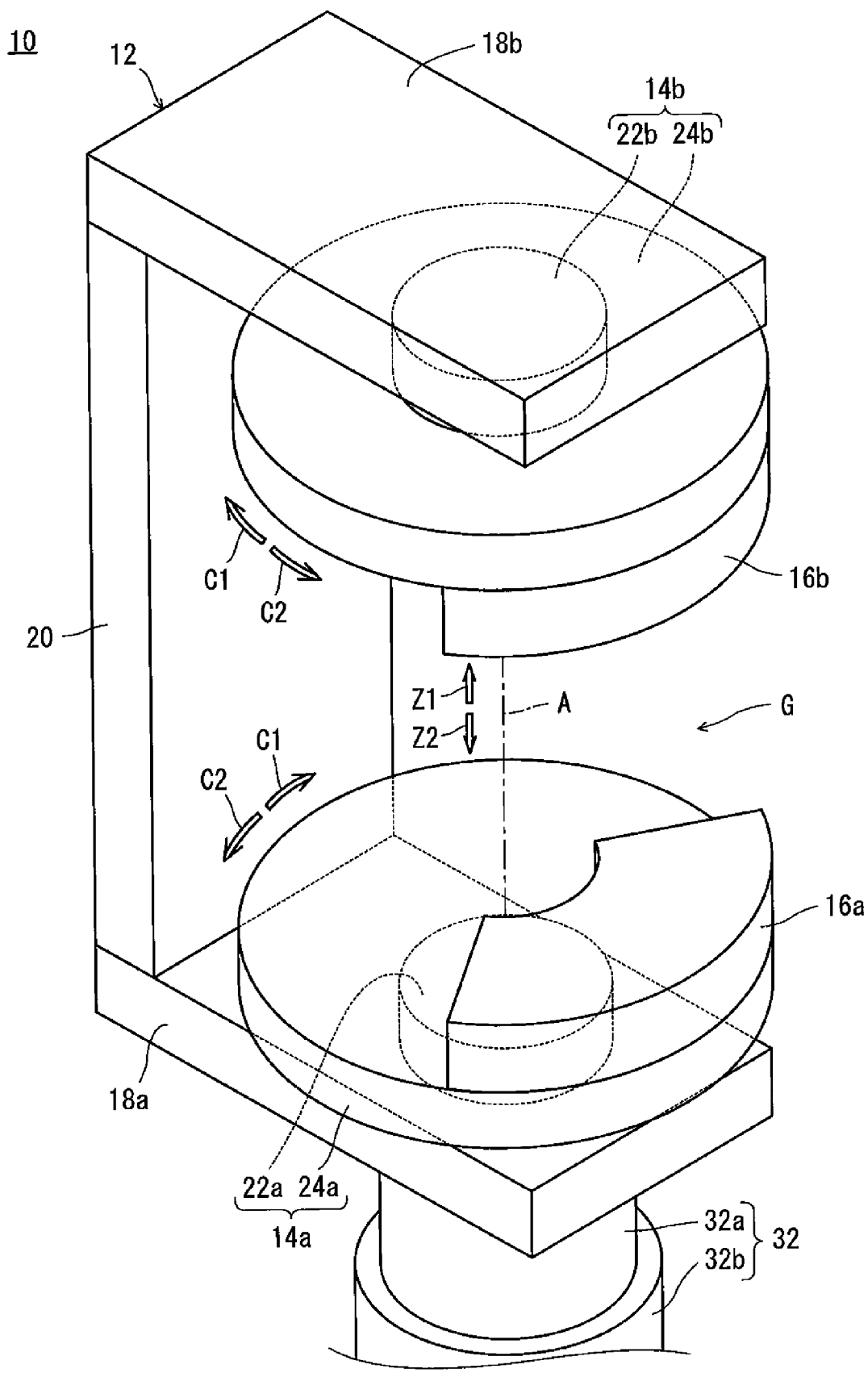
FIG. 1 is a perspective diagram showing an embodiment of the present invention.

LEGEND 10, 10a, 10b Magnetic field generators
14a, 14b, 42a, 42b Drive units
16a, 16b, 48a, 48b, 58a, 58b Permanent magnets
22a, 22b Motors
24a, 24b, 46a, 46b Rotating members
26a, 26b, 38a, 38b, 50a, 50b, 64a, 64b First main surfaces
28a, 28b, 40a, 40b, 52a, 52b, 66a, 66b Second main surfaces
30a, 30b, 54a, 54b Center regions
32 Cylinder
34a, 34b Magnetic field generation units
36a, 36b Assisting permanent magnets
60 First permanent magnet piece
62a, 62b Second permanent magnet pieces
A Predetermined axis

BEST MODE FOR CARRYING OUT THE INVENTION

Hereinafter, embodiments of the present invention will be described with reference to the drawings.

Referring to FIG. 1, a magnetic field generator 10 according to an embodiment of the present invention includes a frame 12 formed into a shape of angled U, a pair of drive units 14a, 14b provided in the frame 12, and a pair of permanent magnets 16a, 16b provided axially of a predetermined axis A (indicated by a dashed-dotted line) with a gap G in between. As understood from FIG. 1, in the present embodiment, the predetermined axis A defines an up-and-down direction (directions indicated by Arrows Z1 and Z2).

The frame 12 includes plate members 18a, 18b opposed to each other in the up-and-down direction, and a connecting member 20 which connects the plate members 18a, 18b with each other. Although there is no specific limitation to the material of which the plate members 18a, 18b and the connecting member 20 are made, it is preferred that the plate members 18a, 18b and the connecting member 20 are made of nonmagnetic material. The plate members 18a, 18b and the connecting member 20 made of nonmagnetic material such as aluminum do not cause adverse affects to a magnetic field in the gap G.

The drive units 14a, 14b are positioned by the frame 12 which functions as disposition means, so as to face each other centering around the predetermined axis A. The drive unit 14a includes a motor 22a and a rotating member 24a. The drive unit 14b includes a motor 22b and a rotating member 24b. The motor 22a which defines a drive power source is fixed on an upper surface of the plate member 18a. The motor 22b is fixed on a lower surface of the plate member 18b. The rotating member 24a is formed like a disc. The rotating member 24a is driven by the motor 22a, and rotates about the predetermined axis A in one of the circumferential directions (directions indicated by Arrows C1 and C2). The rotating member 24b is formed like a disc of the same size as of the rotating member 24a. The rotating member 24b is driven by the motor 22b, and rotates about the predetermined axis A in the direction indicated by Arrow C1 or C2. Although there is no specific limitation to the material of which the plate the rotating members 24a, 24b are made, it is preferred that the rotating members 24a, 24b are made of magnetic material. By using magnetic material such as SS400 for the rotating members 24a, 24b, it becomes possible to raise the operating point of the permanent magnets 16a, 16b.

The permanent magnet 16a is bonded to an upper surface of the rotating member 24a. The permanent magnet 16b is bonded to a lower surface of the rotating member 24b. The permanent magnets 16a, 16b, which are for generation of a magnetic field in the gap G, are each provided by NEOMAX-48BH (made by Hitachi Metals, Ltd.) for example.

Figure 2:
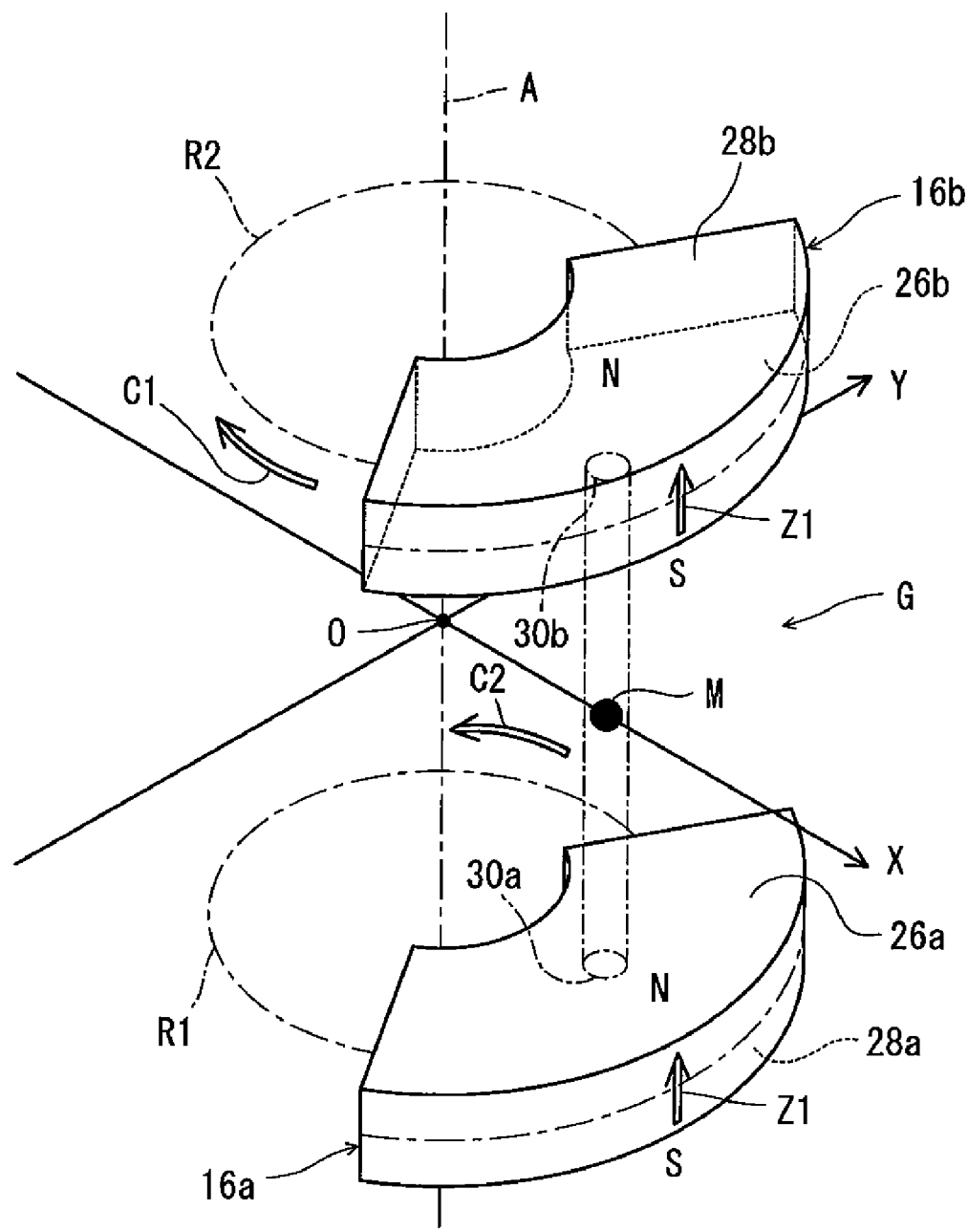
FIG. 2 is a perspective diagram showing a pair of magnetic field generation units used in the embodiment in FIG. 1.

As shown in FIG. 2, each of the permanent magnets 16a, 16b is formed like a segment on an annular locus (having a generally fan-shaped outline). A magnetization direction of the permanent magnet 16a is the direction indicated by Arrow Z1 (vertically upward direction). Therefore, an N-pole is formed on a main surface (hereinafter called first main surface) 26a which is a surface of the permanent magnet 16a on the gap G side. On the other hand, an S-pole is formed on another main surface (hereinafter called second main surface) 28a which is a surface of the permanent magnet 16a facing away from the first main surface 26a. Likewise, a magnetization direction of the permanent magnet 16b is the direction indicated by Arrow Z1. Therefore, an S-pole is formed on a first main surface 26b of the permanent magnet 16b, while an N-pole is formed on a second main surface 28b of the permanent magnet 16b. In other words, the first main surface 26a of the permanent magnet 16a and the first main surface 26b of the permanent magnet 16b each have a magnetic pole of different polarity.

As understood from FIG. 2, the permanent magnet 16a is provided on the rotating member 24a (See FIG. 1) in such a manner that it does not cross the predetermined axis A, nor do any portions thereof oppose to each other to sandwich the predetermined axis A in between. In other words, the permanent magnet 16a is provided on the rotating member 24a so as not to reach the predetermined axis A. Also, the permanent magnet 16a is provided on the rotating member 24a so that a center region 30a (an area indicated by dashed-dotted lines) of the first main surface 26a (N-pole) is off the predetermined axis A. Likewise, the permanent magnet 16b is provided on the rotating member 24b (See FIG. 1) so as not to reach the predetermined axis A. Also, the permanent magnet 16b is provided on the rotating member 24b (See FIG. 1) so that a center region 30b of the first main surface 26b (S-pole) is off the predetermined axis A.

Figure 3:
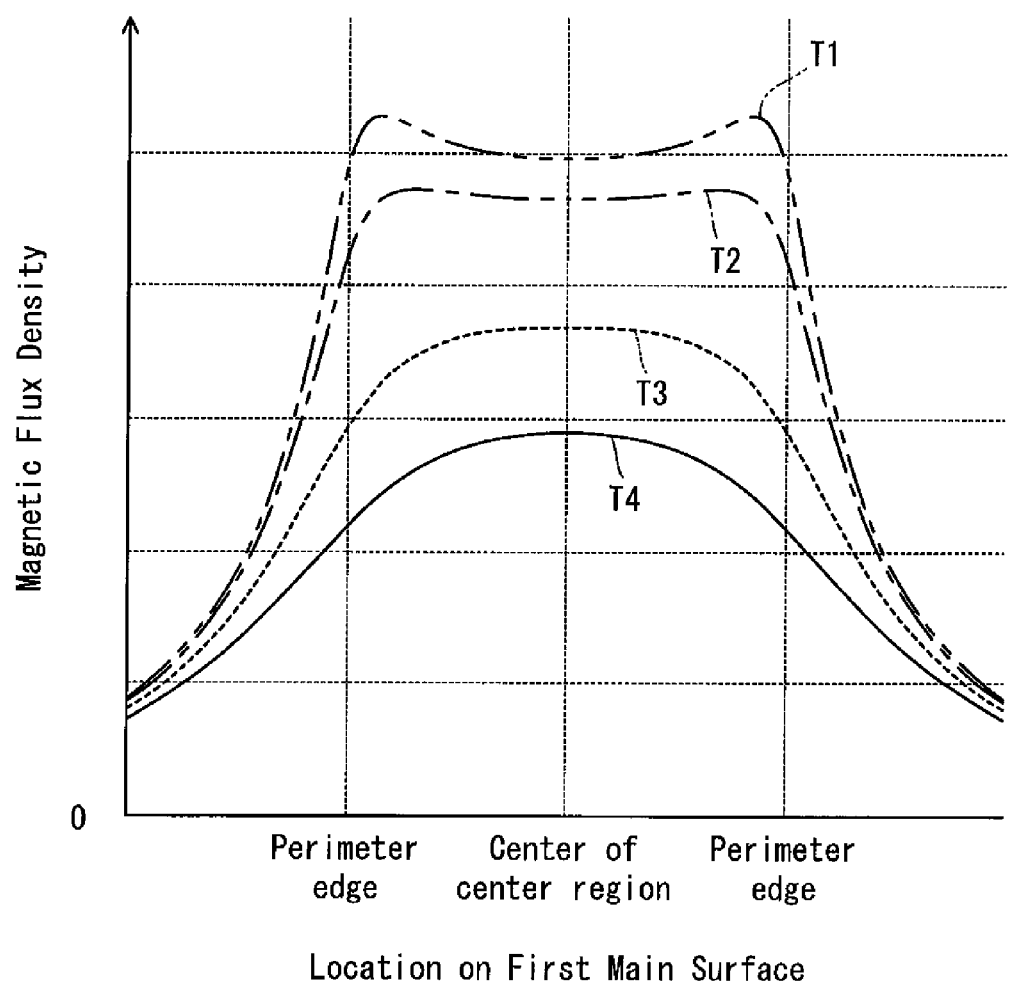
FIG. 3 is a graph showing a relationship between various positions on a first main surface of the magnetic field generation unit and magnetic flux density at positions away from the first main surface of the magnetic field generation unit toward a predetermined plane.

FIG. 3 shows magnetic flux density distribution at locations spaced from the above-described first main surface 26a of the permanent magnet 16a by a distance toward an X-Y plane (See FIG. 2) defined between the first main surfaces 26a, 26b. In FIG. 3, T1, T2, T3 and T4 show magnetic flux density distribution at locations spaced from the first main surface 26a toward the X-Y plane by a distance of 0.7 mm, 1.0 mm, 2.0 mm and 3.0 mm respectively. It should be noted here that the horizontal axis in FIG. 3 represents locations on the first main surface 26a. T1 and T2 indicate that the closer to the first main surface 26a, the greater amount of magnetic flux flowing from near the perimeter region of the first main surface 26a toward near the perimeter region of the second main surface 28a, and that a maximum magnetic flux density is attained at regions corresponding to perimeter regions. However, T3 and T4 indicate that at locations which are relatively far (by a distance of approximately 2.0 mm) from the first main surface 26a, effect of the magnetic flux flowing from the first main surface 26a toward the second main surface 28a is less, and that a maximum magnetic flux density is attained at a portion corresponding to the center region 30a. In the present embodiment, the term "near the first main surface 26a (N-pole)" means a location spaced from the first main surface 26a toward the X-Y plane appropriately to an extent that magnetic flux density distribution is not affected by the magnetic flux which flows from near the perimeter region of the first main surface 26a toward near the perimeter of the second main surface 28a. In the permanent magnet 16a, the magnetic flux density near the first main surface 26a attains a maximum at a location slightly above the center region 30a. The same applies to the permanent magnet 16b, i.e., that the magnetic flux density near the first main surface 26b attains a maximum at a location slightly below the center region 30b.

The permanent magnet 16a revolves on an annular path R1 as the motor 22a rotates the rotating member 24a in the direction indicated by Arrow C1 or C2. Likewise, the permanent magnet 16b revolves on an annular path R2 as the motor 22b rotates the rotating member 24b in the direction indicated by Arrow C1 or C2.

As shown in FIG. 1, a cylinder 32 is connected with the frame 12. The cylinder 32 includes a plunger 32a which has its upper end fixed to a lower surface of the plate member 18a, and a main body 32b which moves the plunger 32a in a direction indicated by Arrow Z1 or Z2. The cylinder 32 moves the frame 12, i.e., the permanent magnets 16a, 16b in the direction indicated by Arrow Z1 or Z2 as the main body 32b moves the plunger 32a in the direction indicated by Arrow Z1 or Z2.

In the present embodiment, the permanent magnets 16a (16b) are the only constituent of the magnetic field generation unit. The drive units 14a, 14b define the first and the second driving means. The cylinder 32 defines the third driving means.

Next, description will cover an example of magnetic field control method for the magnetic field generator 10 which has the construction as described above.

In the magnetic field generator 10, the permanent magnets 16a, 16b are revolved to move a local maximum point of the magnetic field intensity on a predetermined plane which crosses the predetermined axis A vertically between the permanent magnets 16a, 16b. Herein, description will be made for a combined case where a first operation of revolving the permanent magnet 16a relatively to the permanent magnet 16b is combined with a second operation of revolving the permanent magnets 16a, 16b in the same direction by the same angle.

As shown in FIG. 2, the predetermined plane herein is provided by an X-Y plane which is defined by an axis X that is orthogonal to the predetermined axis A and passes through the middle point between the paths R1, R2, and an axis Y that is orthogonal to the predetermined axis A and to the axis X. Hereinafter, an intersection made by the predetermined axis A, the axis X and the axis Y will be called the intersection O, and a direction indicated by Arrows of the axis X and of the axis Y will be called plus direction whereas the opposite directions will be called minus direction.

On the X-Y plane, a position sandwiched between the center region 30a which represents the region where magnetic flux density near the first main surface 26a attains a maximum and the center region 30b which represents the region where magnetic flux density near the first main surface 26b attains a maximum is a position where a maximum amount of magnetic flux flows through. Therefore, a local maximum point M of the magnetic field intensity on the X-Y plane exists at the position sandwiched between the center regions 30a, 30b. FIG. 2 shows a state where the first main surfaces 26a, 26b face each other squarely (overlapping completely), and the axis X is sandwiched by the center regions 30a, 30b on the plus side of the intersection O. In other words, FIG. 2 shows a state where the local maximum point M is on the axis X, on the plus side of the intersection O and at the farthest position from the intersection O.

First, with reference to FIG. 2 as well as FIG. 4 through FIG. 7, description will be made for an example of the first operation in which the permanent magnet 16a is revolved relatively to the permanent magnet 16b. Herein, the drive unit 14a (See FIG. 1) will revolve the permanent magnet 16a in the direction indicated by Arrow C2 (circumferentially counter-clockwise), from the position illustrated in FIG. 2 as being an initial position. Simultaneously with this, the drive unit 14b (See FIG. 1) will revolve the permanent magnet 16b in the direction indicated by Arrow C1 (circumferentially clockwise) by the same angle as the permanent magnet 16a, from the position illustrated in FIG. 2 as being an initial position. In other words, this is an example of the first operation in which the permanent magnets 16a, 16b are revolved in opposite directions by the same angle.

Figure 4:
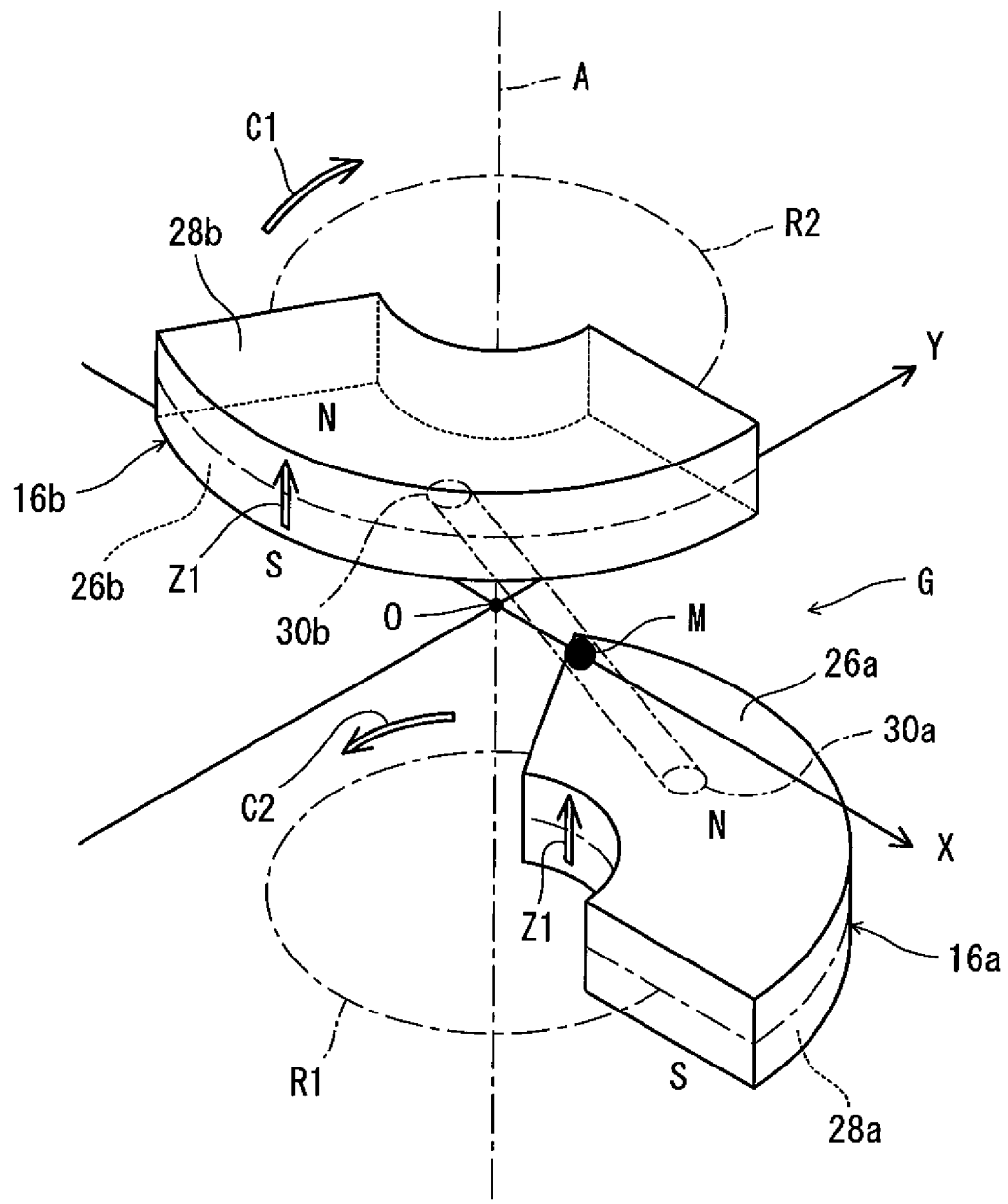
FIG. 4 is a perspective diagram showing a state where each of the magnetic field generation units in the pair has been revolved by 60 degrees in mutually opposite directions from the state in FIG. 2.

As shown in FIG. 4, by revolving the permanent magnets 16a, 16b in opposite directions by the same angle, the permanent magnets 16a, 16b move away from each other (overlapping less), and the position on the X-Y plane sandwiched by the center regions 30a, 30b moves on the axis X in the minus direction toward the intersection O. Therefore, the local maximum point M makes a rectilinear travel on the axis X in the minus direction toward the intersection O. It should be noted here that FIG. 4 shows a state where the permanent magnets 16a, 16b are revolved by 60 degrees in mutually opposite directions from their respective positions in FIG. 2.

Figure 5:
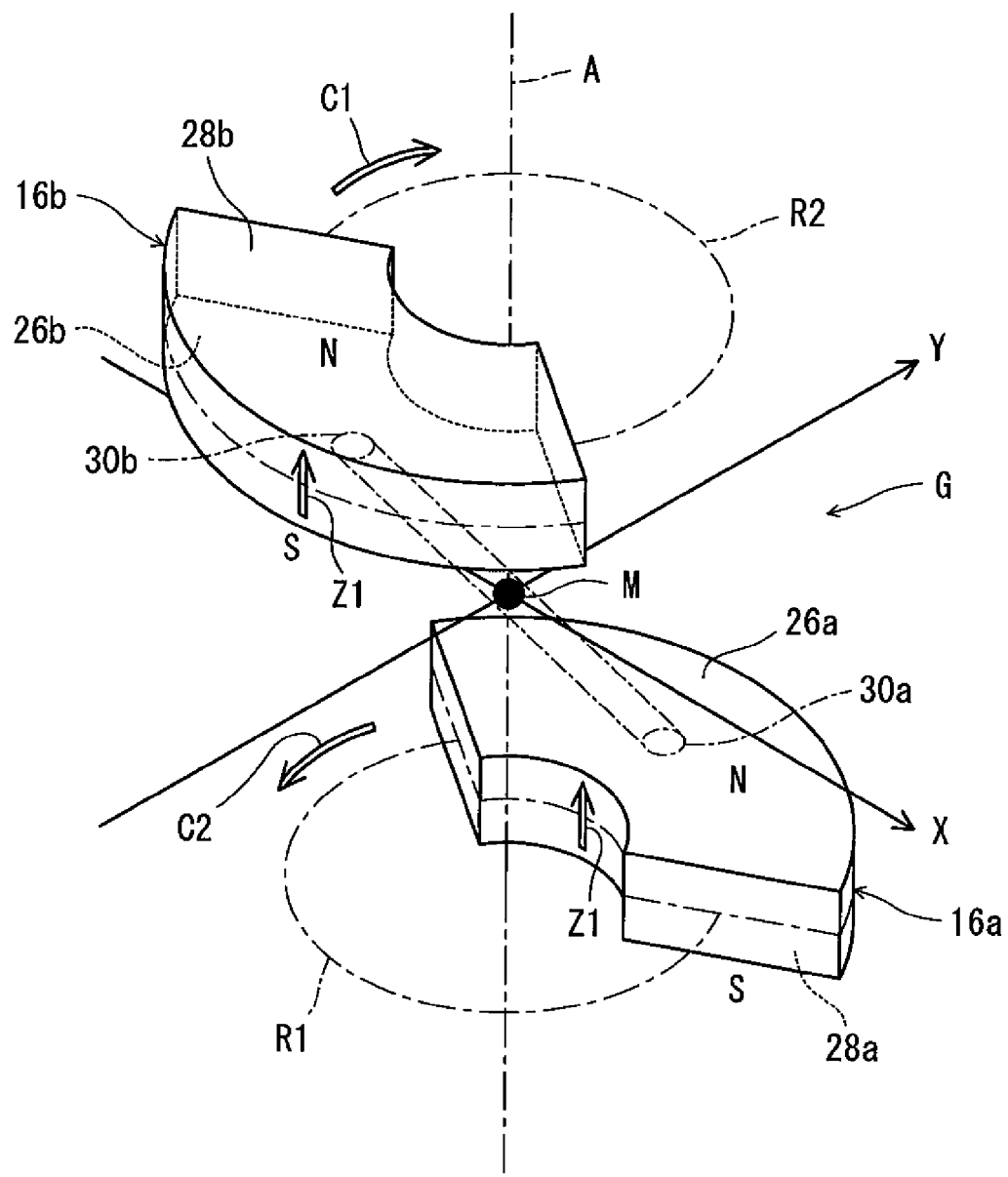
FIG. 5 is a perspective diagram showing a state where each of the magnetic field generation units in the pair has been revolved by 90 degrees in mutually opposite directions from the state in FIG. 2.

Then, as shown in FIG. 5, in a state where the permanent magnets 16a, 16b have been revolved by 90 degrees in mutually opposite directions from their respective positions in FIG. 2, the intersection O is sandwiched by the center regions 30a, 30b, with the local maximum point M being on the intersection O. By revolving the permanent magnets 16a, 16b further from the state in FIG. 5, the permanent magnets 16a, 16b come closer to each other, and the local maximum point M makes a rectilinear travel on the axis X in the minus direction on the axis X from the intersection O.

Figure 6:
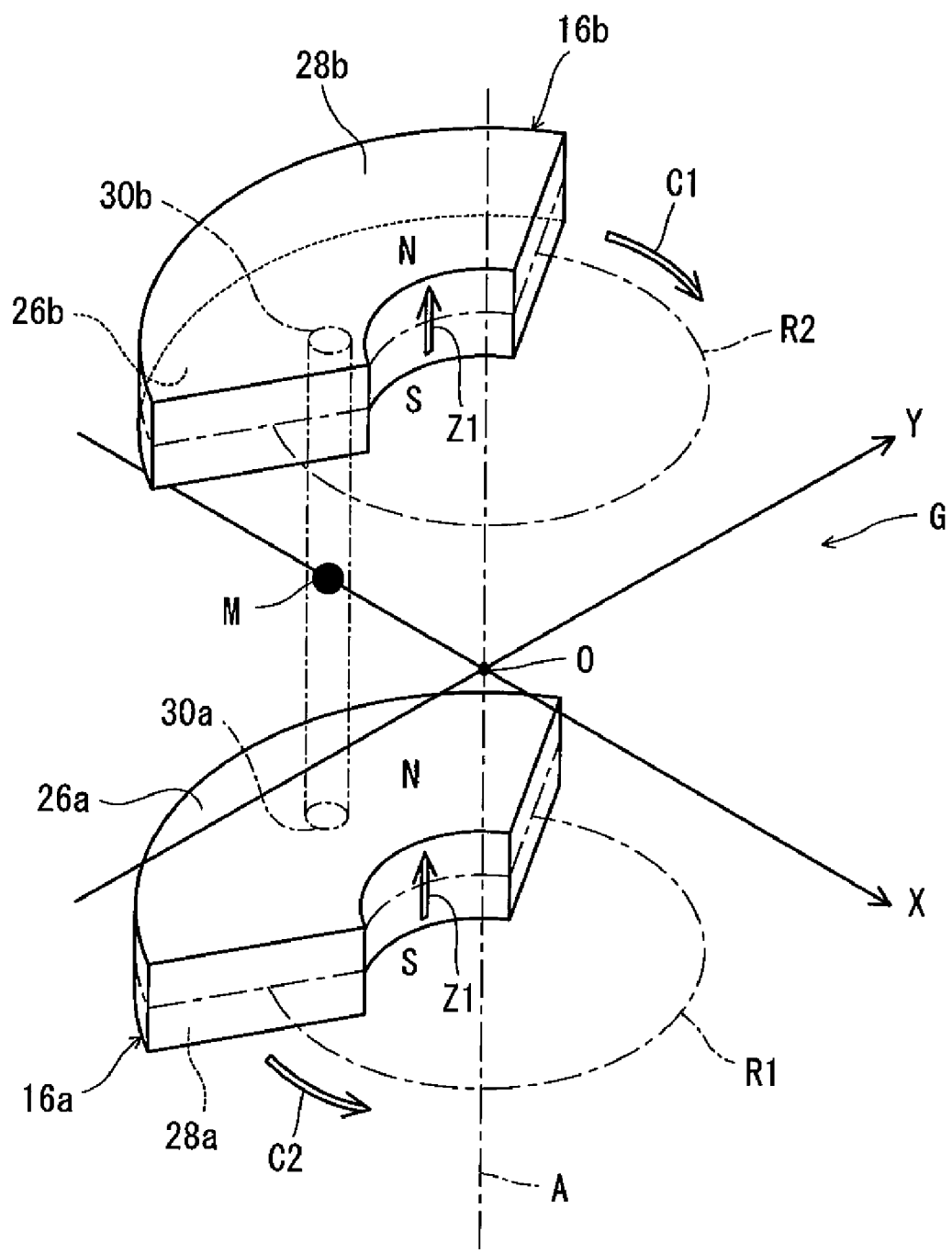
FIG. 6 is a perspective diagram showing a state where each of the magnetic field generation units in the pair has been revolved by 180 degrees in mutually opposite directions from the state in FIG. 2.

Then, as shown in FIG. 6, in a state where the permanent magnets 16a, 16b have been revolved by 180 degrees in mutually opposite directions from their respective positions in FIG. 2, the first main surfaces 26a, 26b face squarely with each other, with the center regions 30a, 30b sandwiching the axis X on the minus side of the intersection O. In other words, the local maximum point M is on the axis X, on the minus side of the intersection O and at the farthest position from the intersection O. Then, as the permanent magnets 16a, 16b are further revolved, the permanent magnets 16a, 16b move away from each other again, moving the local maximum point M on the axis X in the plus direction toward the intersection O.

Figure 7:
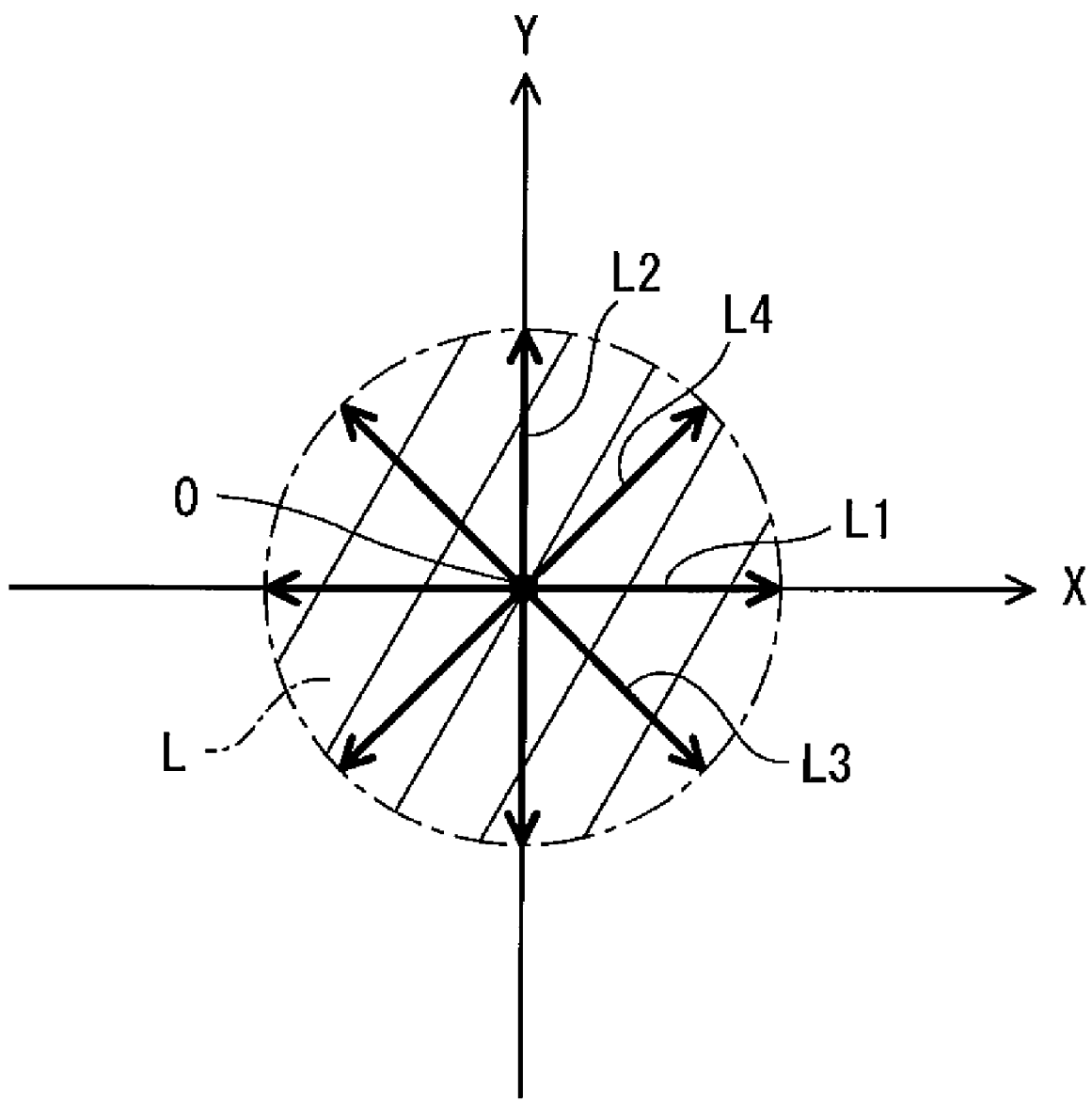
FIG. 7 is a perspective diagram showing a range in which a local maximum point moves.

In the first operation in which the permanent magnets 16a, 16b are revolved by the same angle in mutually opposite directions as described, the local maximum point M makes a rectilinear travel on the axis X within a range indicated by L1 in FIG. 7.

Next, with reference to FIG. 2 and FIG. 8, description will be made for the second operation in which the permanent magnets 16a, 16b are revolved in the direction indicated by Arrow C1 or C2 by the same angle. Herein, the position illustrated in FIG. 2 will be an initial position, and the drive units 14a, 14b (See FIG. 1) will revolve the permanent magnets 16a, 16b respectively, in the direction indicated by Arrow C1 or C2 by the same angle.

Figure 8:
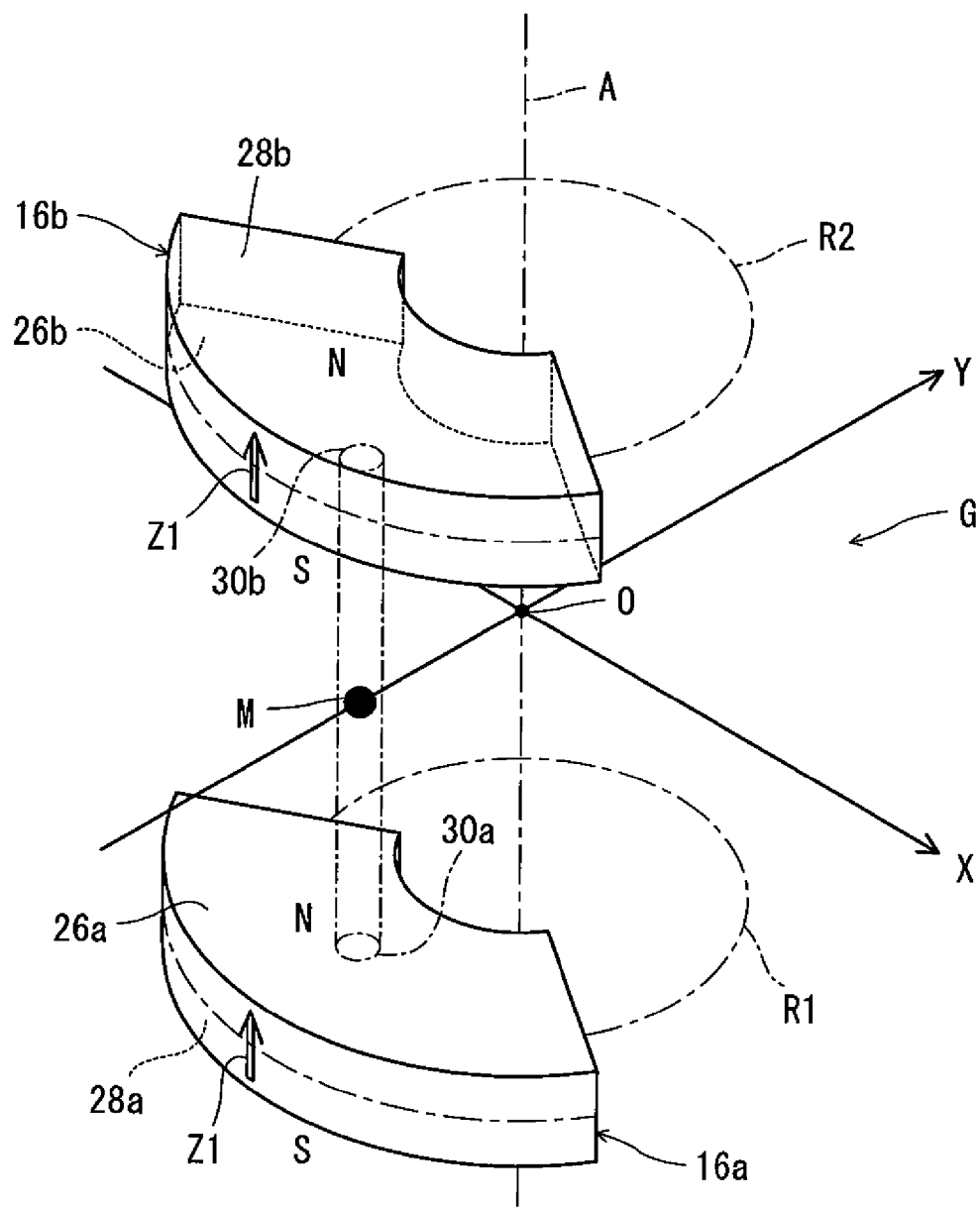
FIG. 8 is a perspective diagram showing a state where each of the magnetic field generation units in the pair has been revolved by 90 degrees in the same direction from the state in FIG. 2.

FIG. 8 shows a state where the permanent magnets 16a, 16b are revolved by 90 degrees in the direction indicated by Arrow C1 or by 270 degrees in the direction indicated by Arrow C2 from the state in FIG. 2. Under the state in FIG. 8, the first main surfaces 26a, 26b face squarely with each other, with the center regions 30a, 30b sandwiching the axis Y on the minus side of the intersection O. Therefore, the local maximum point M is on the axis Y, on the minus side of the intersection O and at the farthest position from the intersection O. The distance from the intersection O to the local maximum point M in the state in FIG. 2 is the same as in the state in FIG. 8. By revolving the permanent magnets 16a, 16b in the same direction by the same angle as described, the local maximum point M moves along a circular path on the X-Y plane while keeping a constant distance from the intersection O to the local maximum point M (See FIG. 7). By revolving the permanent magnets 16a, 16b in mutually opposite directions by the same angle from the position illustrated in FIG. 8 as being an initial position, the local maximum point M makes a rectilinear travel on the axis Y within a range indicated by L2 in FIG. 7.

By combining the first operation in which the permanent magnets 16a, 16b are revolved in mutually opposite directions by the same angle and the second operation in which the permanent magnets 16a, 16b are revolved in the same direction by the same angle as described, it is possible to move the local maximum point M to any position within a predetermined area L on the X-Y plane (See FIG. 7). It should be noted here that L3 in FIG. 7 indicates a range of travel of the local maximum point M when the permanent magnets 16a, 16b are revolved in mutually opposite directions by the same angle, from an initial position attained when the permanent magnets 16a, 16b were revolved in the direction indicated by Arrow C1 by 45 degrees or in the direction indicated by Arrow C2 by 135 degrees from the position illustrated in FIG. 2. Likewise, L4 indicates a range of travel of the local maximum point M when the permanent magnets 16a, 16b are revolved in mutually opposite directions by the same angle, from an initial position attained when the permanent magnets 16a, 16b were revolved in the direction indicated by Arrow C2 by 45 degrees or in the direction indicated by Arrow C1 by 135 degrees from the position illustrated in FIG. 2.

Further, in the magnetic field generator 10, by causing the cylinder 32 (See FIG. 1) to move the frame 12, i.e., the permanent magnets 16a, 16b, in the direction indicated by Arrow Z1 or Z2, it is possible to move the X-Y plane in the direction indicated by Arrow Z1 or Z2. Therefore, by combining revolution of the permanent magnets 16a, 16b and axial travel of the permanent magnets 16a, 16b along the predetermined axis A, it is possible to move the local maximum point M to any position within a predetermined space.

According to the magnetic field generator 10 as described above, it is possible to move the local maximum point M to any position within the predetermined range L on the X-Y plane (See FIG. 7) by combining the first operation in which the permanent magnets 16a, 16b are revolved in mutually opposite directions by the same angle and the second operation in which the permanent magnets 16a, 16b are revolved in the same direction by the same angle. In other words, according to the magnetic field generator 10, it is possible to move the local maximum point M to any position easily within the predetermined range L on the X-Y plane, by only a single operation, i.e., revolution of the permanent magnets 16a, 16b. Therefore, the magnetic field generator 10 can be used suitably in magnetic guide systems for guiding such objects as medical instruments and drugs which contain magnetic material, to a target position inside the body.

By combining a revolution of the permanent magnets 16a, 16b with a travel of the permanent magnets 16a, 16b in the direction indicated by Arrow Z1 or Z2, it is possible to move the local maximum point M to any position within a predetermined space. This makes possible for the magnetic guide system to guide the object to a target position more reliably.

The magnetic field generation unit is constituted by the permanent magnets 16a, 16b. Thus, it is possible to simplify the construction of the magnetic field generation unit, i.e., constitution of the magnetic field generator 10. Since no energy supply is required to generate the magnetic field, it is possible to lower running cost.

By using small, segment-shaped permanent magnets 16a, 16b disposed on an annular locus not to reach the predetermined axis A, it becomes possible to reduce the weight and manufacturing cost of the magnetic field generator 10.

Figure 9:
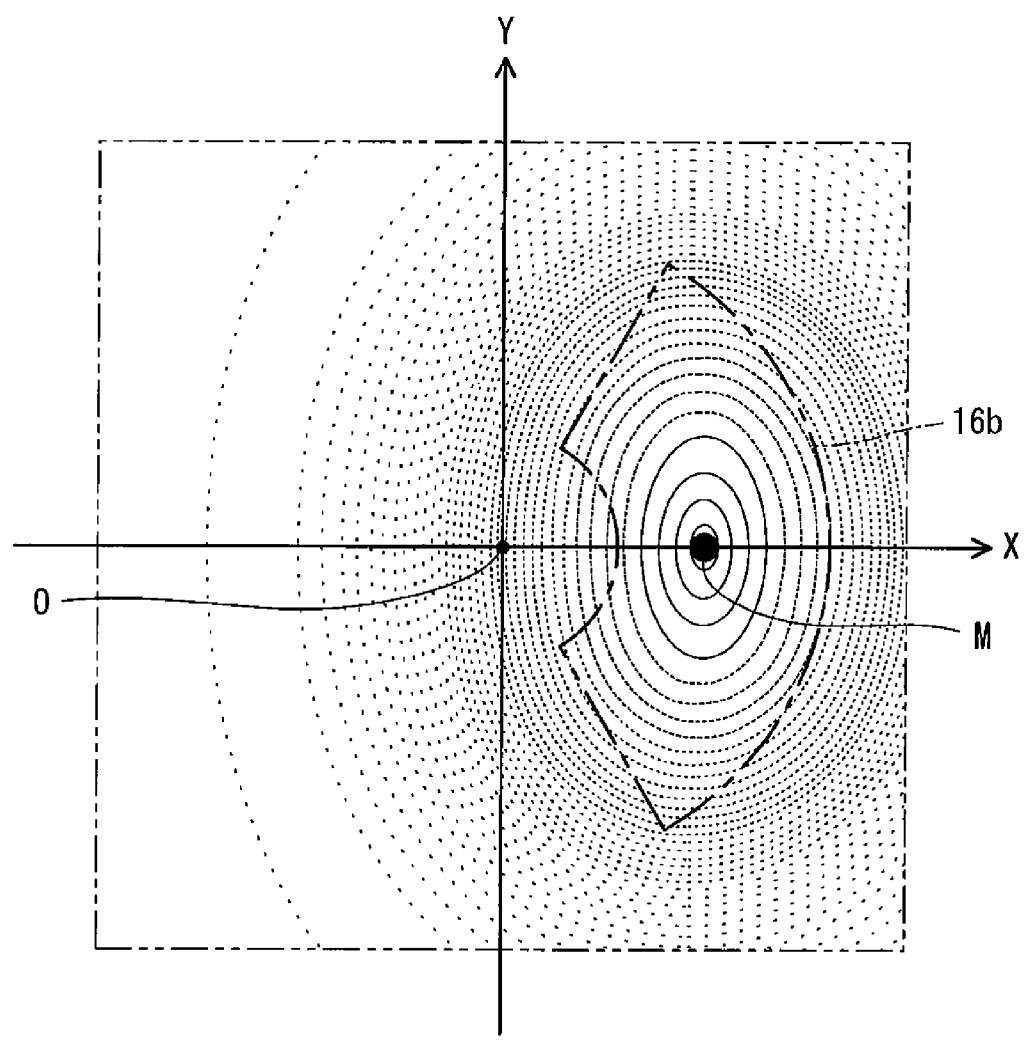
FIG. 9 is a diagram showing magnetic field intensity distribution on an X-Y plane under the state in FIG. 2.

For reference, in the magnetic field generator 10, the distance between the center regions 30a, 30b increases as the local maximum point M is brought closer to the intersection O. Therefore, the magnetic field intensity of the local maximum point M decreases as the local maximum point M comes closer to the intersection O. FIG. 9 shows distribution of the magnetic field intensity on the X-Y plane under the state in FIG. 2, and FIG. 10 shows distribution of the magnetic field intensity on the X-Y plane under the state in FIG. 5. In FIG. 9 and FIG. 10, intensity of the magnetic field on the X-Y plane is indicated by different types of contour lines which surround annularly around the local maximum point M. Specifically, the magnetic field intensity increases as the contour line becomes more like a solid line from a broken line (as the line is closer to the center of circles). From comparison between FIG. 9 and FIG. 10, it is understood that the magnetic field intensity is smaller even around the local maximum point M in FIG. 10 because of a longer distance between the center regions 30a, 30b. Further, FIG. 10 shows wider gap between contours than in FIG. 9, indicating that the magnetic field gradient is smaller.

Figure 11:
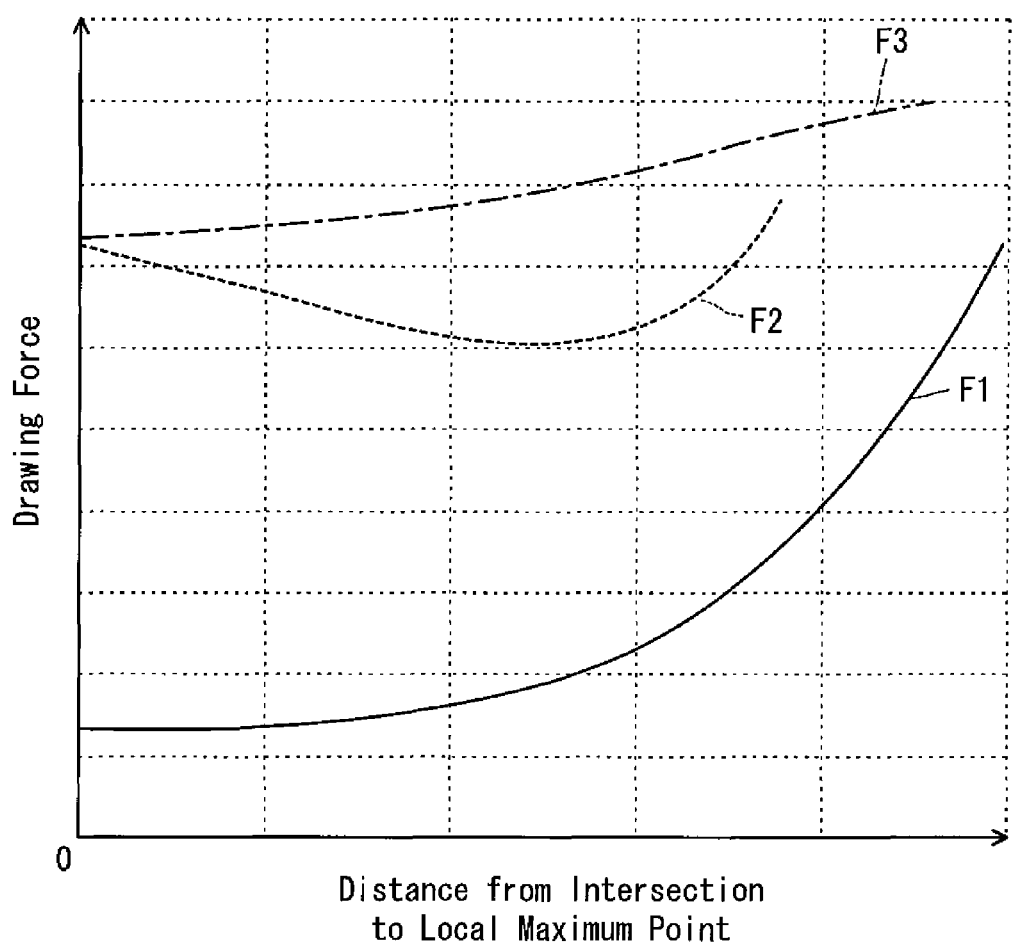
FIG. 11 is a graph showing a relationship between position and drawing power of a local maximum point.

As described, the magnetic field gradient on the X-Y plane decreases and the magnetic field intensity of the local maximum point M decreases as the local maximum point M comes closer to the intersection O. As a result, a force (hereinafter called drawing force) by which the target magnetic material is drawn to the local maximum point M in the magnetic field generated by the permanent magnets 16a, 16b also decreases as the local maximum point M comes closer to the intersection O. The relationship between the distance from the intersection O to the local maximum point M and the drawing force (magnetic force) in the magnetic field generator 10 is shown in FIG. 11 as F1. From F1, it is understood that the drawing force also decreases as the local maximum point M comes closer to the intersection O.

It should be noted here that in the magnetic field generator 10 described above, an example of the first operation was revolving the permanent magnets 16a, 16b in mutually opposite directions by the same angle. However, the first operation is not limited to this. For example, the permanent magnets 16a, 16b may be revolved in mutually opposite directions by different angles, or the permanent magnets 16a, 16b may be revolved in the same direction by different angles. Further, only one of the permanent magnets 16a, 16b may be revolved. For example, in a case where only the permanent magnet 16b is revolved in the direction indicated by Arrow C2 from the state in FIG. 2, the local maximum point M moves along an arc which bulges toward the plus side of the axis Y, reaches the intersection O, then moves along an arc bulging toward the minus side of the axis Y from the intersection O and returns to the position in the FIG. 2.

Next, description will be made for a magnetic field generator 10a as another embodiment of the present invention, with reference to FIG. 12 and FIG. 13. The magnetic field generator 10a uses magnetic field generation units 34a, 34b in order to reduce the magnetic field intensity drop at the local maximum point M associated with the approach to the intersection O.

Figure 12:
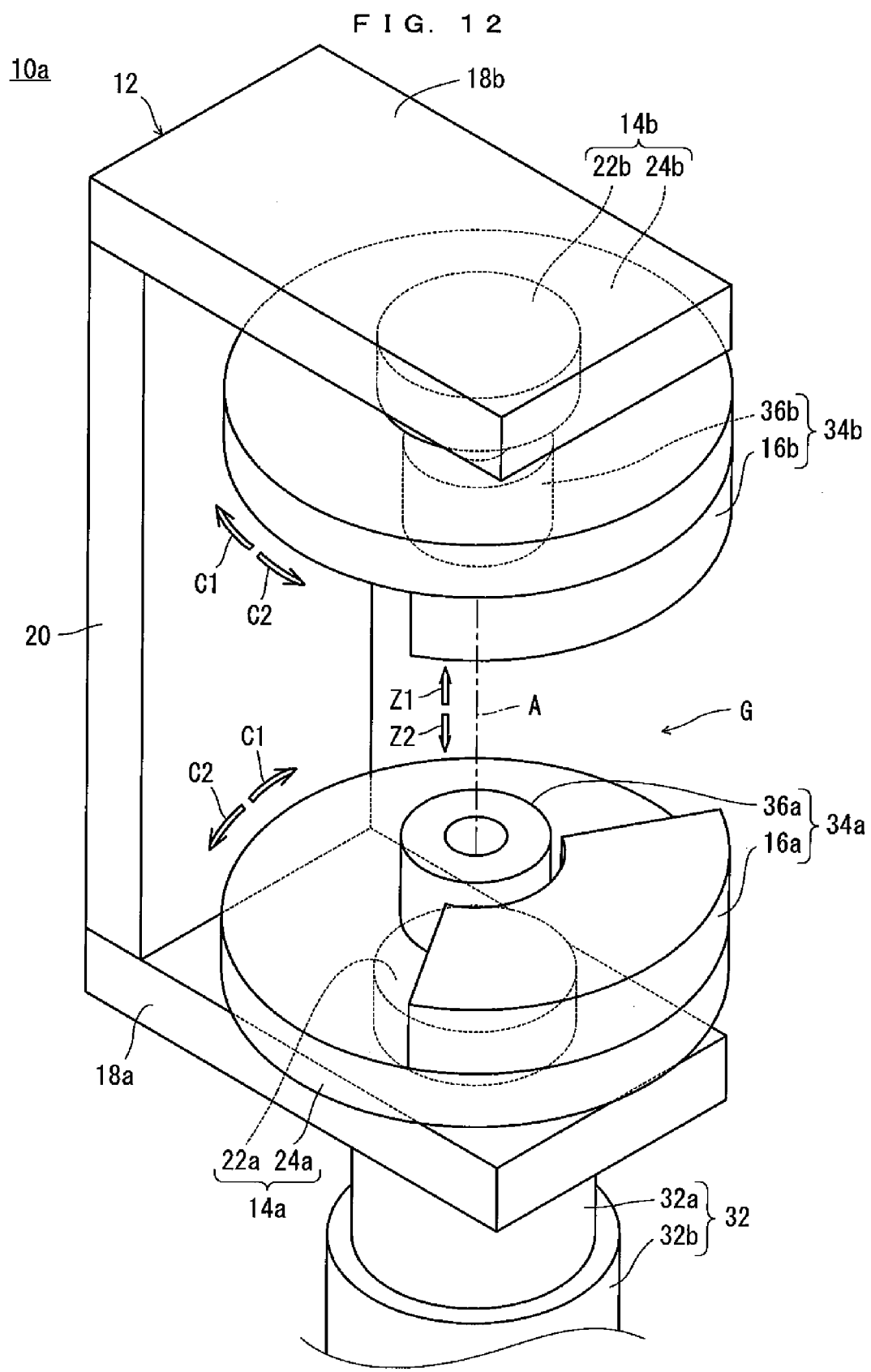
FIG. 12 is a perspective diagram showing another embodiment of the present invention.

As shown in FIG. 12, the magnetic field generation unit 34a includes a permanent magnet 16a and an assisting permanent magnet 36a. The magnetic field generation unit 34b includes a permanent magnet 16b and an assisting permanent magnet 36b. Except that the magnetic field generation units 34a, 34b include the assisting permanent magnets 36a, 36b, this embodiment is the same as the magnetic field generator 10, and repetitive description will not be made hereinafter.

Figure 13:
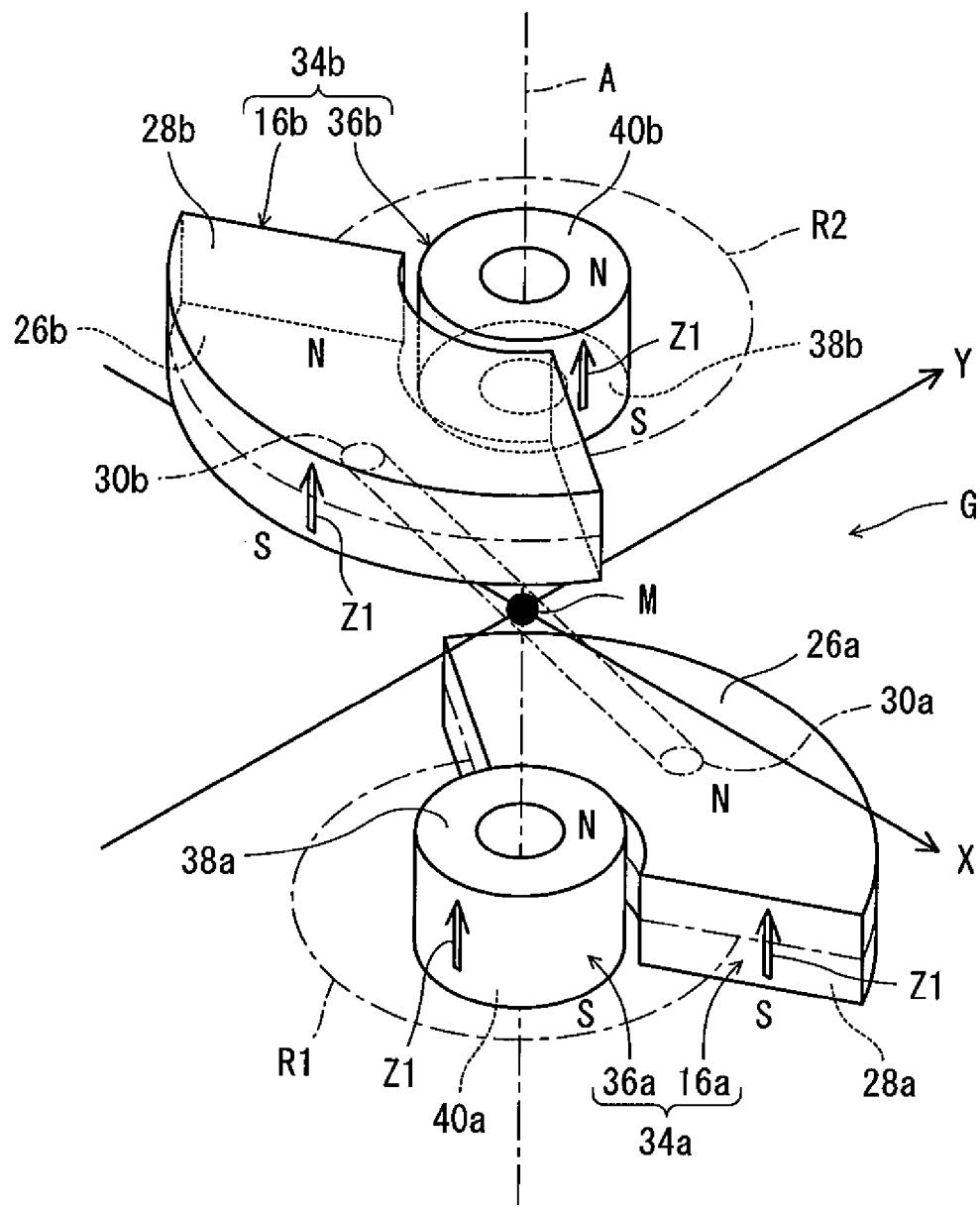
FIG. 13 is a perspective diagram showing a pair of magnetic field generation units used in the embodiment in FIG. 12.

As shown in FIG. 13, the assisting permanent magnet 36a of the magnetic field generation unit 34a is cylindrical. The assisting permanent magnet 36a is fixed to an upper surface of the rotating member 24a (See FIG. 12) so that its center is passed by the predetermined axis A. The assisting permanent magnet 36b of the magnetic field generation unit 34b has the same shape and dimensions as the assisting permanent magnet 36a. The assisting permanent magnet 36b is fixed to a lower surface of the rotating member 24b (See FIG. 12) so that its center is passed by the predetermined axis A. The assisting permanent magnet 36a rotates about the predetermined axis A as the rotating member 24a rotates. The assisting permanent magnet 36b rotates about the predetermined axis A as the rotating member 24b rotates. The assisting permanent magnet 36a which rotates about the predetermined axis A does not make a travel with the rotation of the rotating member 24a. This also applies to the assisting permanent magnet 36b.

The assisting permanent magnets 36a, 36b are each magnetized in the direction indicated by Arrow Z1. Therefore, an N-pole is formed on a first main surface 38a of the assisting permanent magnet 36a, and an S-pole is formed on a second main surface 40a of the assisting permanent magnet 36a. On the other hand, an S-pole is formed on a first main surface 38b of the assisting permanent magnet 36b, and an N-pole is formed on a second main surface 40b of the assisting permanent magnet 36b. The assisting permanent magnets 36a, 36b are each provided by NEOMAX-48BH (made by Hitachi Metals, Ltd.) for example.

According to the magnetic field generator 10a as described, the assisting permanent magnets 36a, 36b which do not make a travel from a predetermined position provides a magnetic flux that is not smaller than a predetermined intensity, near the intersection O on the X-Y plane regardless of the position of the permanent magnets 16a, 16b. Therefore, it is possible to reduce magnetic field gradient drop and magnetic field intensity drop at the local maximum point M on the X-Y plane even if the local maximum point M is moved to a vicinity of the intersection O.

FIG. 14 shows distribution of the magnetic field intensity on the X-Y plane under the state in FIG. 13. Comparison between FIG. 10 and FIG. 14 shows that it is possible to increase the magnetic field gradient on the X-Y plane and increase the magnetic field intensity at and around the local maximum point M in the magnetic field generator 10a as compared to the magnetic field generator 10, by providing the assisting permanent magnets 36a, 36b. A relationship between the distance from the intersection O to the local maximum point M and the drawing force in the magnetic field generator 10a is shown in FIG. 11 as F2. From F2, it is understood that a drop in the drawing force even when the local maximum point M comes to a vicinity of the intersection O is reduced.

Next, description will be made for a magnetic field generator 10b as still another embodiment of the present invention, with reference to FIG. 15 and FIG. 16.

The magnetic field generator 10b uses a frame 12a instead of the frame 12, and drive units 42a, 42b instead of the drive units 14a, 14b. The frame 12a uses plate members 44a, 44b which have a longer longitudinal dimension than the plate members 18a, 18b. The drive unit 42a uses a disc-like rotating member 46a which is larger than the rotating member 24a. The drive unit 42b uses a rotating member 46b of the same shape and dimensions as the rotating member 46a. In addition, permanent magnets 48a, 48b are used as a pair of magnetic field generation units. All the other aspects are the same as the magnetic field generators 10, 10a, so repetitive description will not be made hereinafter.

Figure 16:
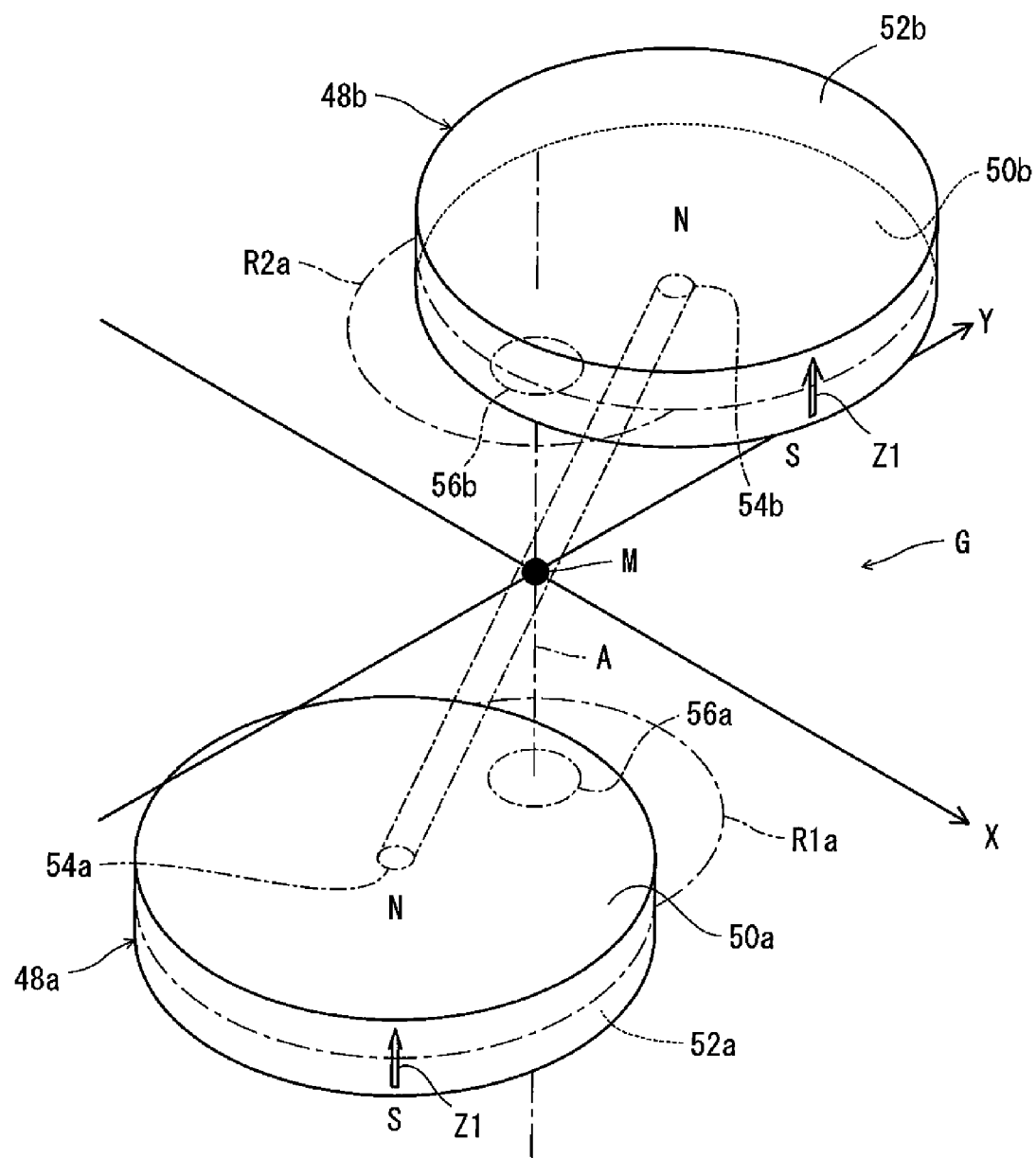
FIG. 16 is a perspective diagram showing a pair of magnetic field generation units used in the embodiment in FIG. 15.

As shown in FIG. 16, the permanent magnets 48a, 48b are magnetized in the direction indicated by Arrow 11. Therefore, an N-pole is formed on a first main surface 50a of the permanent magnet 48a, and an S-pole is formed on a second main surface 52a of the permanent magnet 48a. On the other hand, an S-pole is formed on a first main surface 50b of the permanent magnet 48b, and an N-pole is formed on a second main surface 52b of the permanent magnet 48b. The permanent magnets 48a, 48b are each provided by NEOMAX-48BH (made by Hitachi Metals, Ltd.) for example.

The permanent magnets 48a, 48b are circular. In the present embodiment, each of the permanent magnets 48a, 48b has a disc-like shape. The permanent magnet 48a is fixed to an upper surface of the rotating member 46a (See FIG. 15)

so that a center region 54a (indicated by dashed-dotted lines) of the first main surface 50a is off the predetermined axis A yet an edge region 56a of the first main surface 50a reaches the predetermined axis A. Likewise, the permanent magnet 48b is disc-like. The permanent magnet 48b is fixed to a lower surface of the rotating member 46b (See FIG. 15) so that a center region 54b of the first main surface 50b is off the predetermined axis A yet an edge region 56b of a first circumferential surface 50b reaches the predetermined axis A. In the permanent magnet 48a, the magnetic flux density near the first main surface 50a attains a maximum at a location slightly above the center region 54a. The same applies to the permanent magnet 48b, i.e., that the magnetic flux density near the first main surface 50b attains a maximum at a location slightly below the center region 54b.

The permanent magnet 48a revolves on an annular path R1a as the motor 22a rotates the rotating member 46a in the direction indicated by Arrow C1 or C2. Likewise, the permanent magnet 48b revolves on an annular path R2a as the motor 22b rotates the rotating member 46b in the direction indicated by Arrow C1 or C2.

The permanent magnets 48a, 48b provided in such an arrangement as described above make the intersection O always sandwiched between an edge region 56a of the first main surface 50a and an edge region 56b of the first main surface 50b.

According to the magnetic field generator 10b as described, a magnetic flux that is not smaller than a predetermined intensity is given near the intersection O regardless of the position of the permanent magnets 48a, 48b since the intersection O is sandwiched between the edge regions 56a, 56b. Therefore, it is possible to reduce magnetic field gradient drop on the X-Y plane as well as magnetic field intensity drop of the local maximum point M even when the local maximum point M is moved to a vicinity of the intersection O, as in the magnetic field generator 10a.

Figure 17:
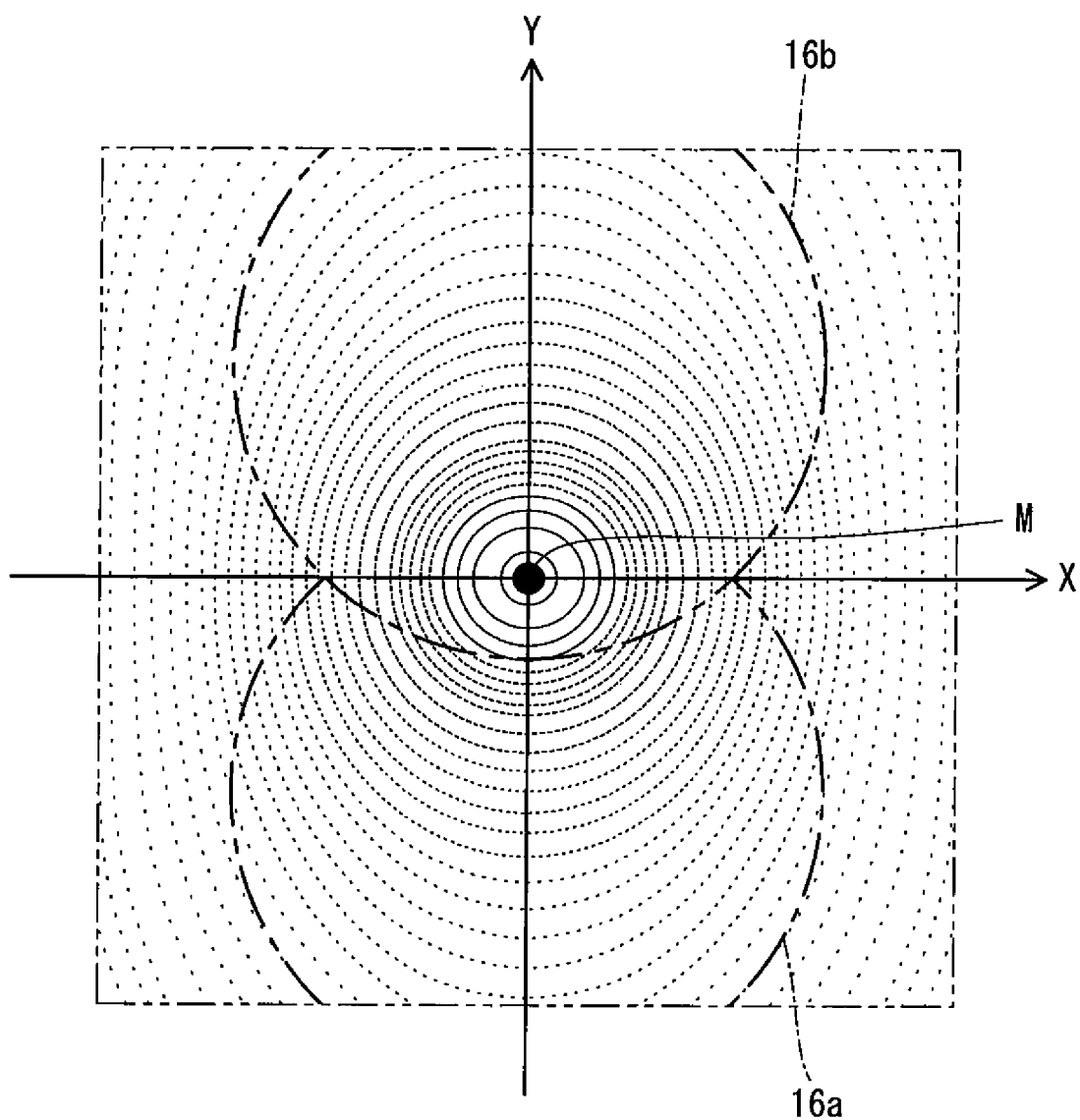
FIG. 17 is a diagram showing magnetic field intensity distribution on the X-Y plane under the state in FIG. 16.

FIG. 17 shows distribution of the magnetic field intensity on the X-Y plane under the state in FIG. 16. Comparison between FIG. 10 and FIG. 17 shows that it is possible to increase the magnetic field gradient on the X-Y plane and increase the magnetic field intensity at the local maximum point M in the magnetic field generator 10b than in the magnetic field generator 10, since the intersection O is sandwiched between the edge regions 56a, 56b of the permanent magnets 48a, 48b. A relationship between the distance from the intersection O to the local maximum point M and the drawing force in the magnetic field generator 10b is shown in FIG. 11 as F3. From F3, it is understood that drop in the drawing force even when the local maximum point M comes to a vicinity of the intersection O is reduced.

Next, description will cover an example of magnetic field control method for the magnetic field generator 10b.

In this example, the permanent magnets 48a, 48b were provided by NEOMAX-48SBH (made by Hitachi Metals, Ltd.) of a disc-like shape which had the first main surface and the second main surface of a 70 mm radius and a thickness of a 24 mm. The distance between the first main surfaces 50a, 50b in the direction indicated by Arrow Z1 was set to 100 mm (See FIG. 16). In other words, the gap G was set to 100 mm. In this case, the predetermined area L (See FIG. 18) of travel for the local maximum point on the X-Y plane had a diameter of 100 mm.

Figure 15:
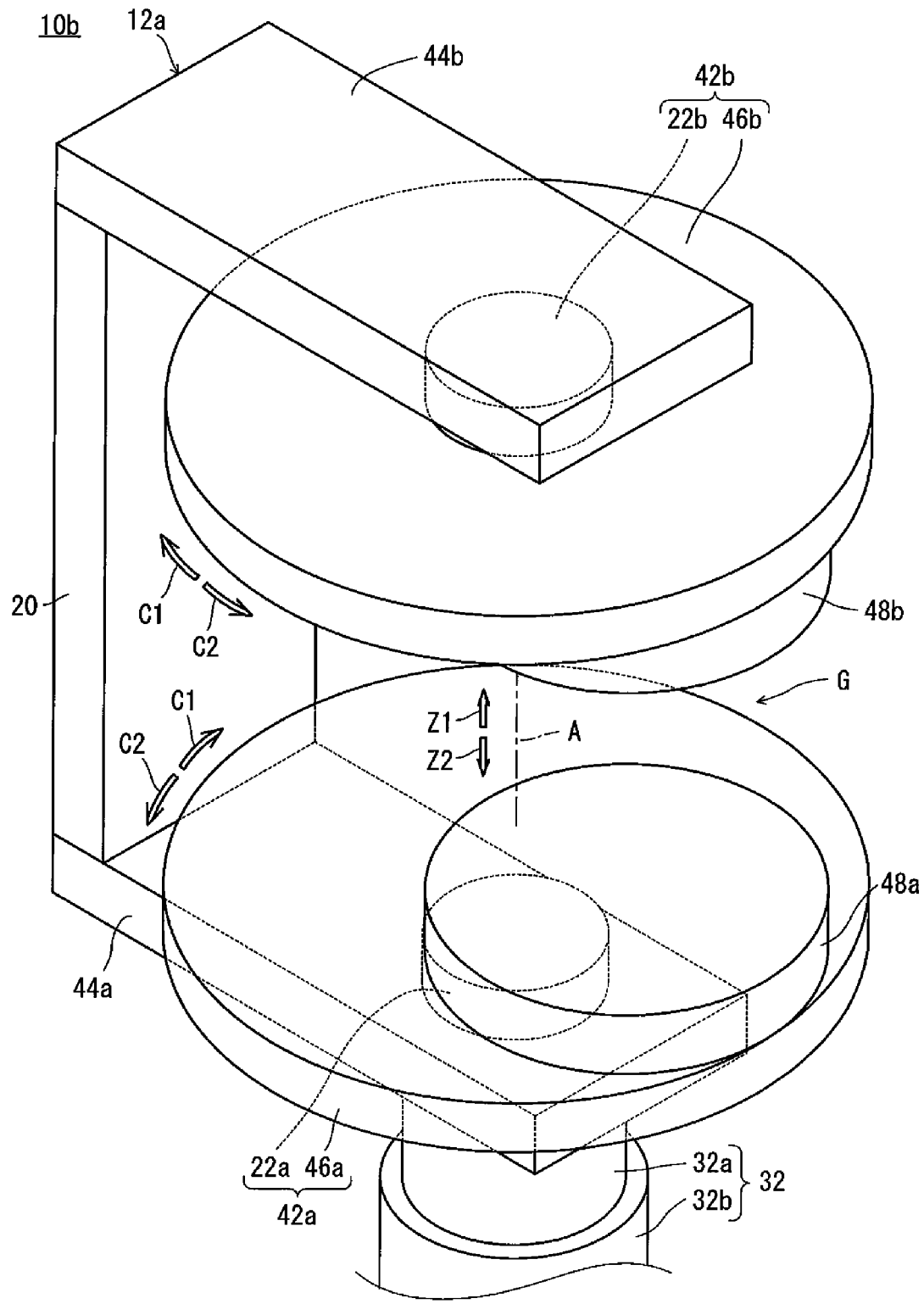
FIG. 15 is a perspective diagram showing still another embodiment of the present invention.

In the description, the permanent magnets 48a, 48b will be revolved from a state where the permanent magnets 48a, 48b are faced squarely with each other (See FIG. 15). In other words, the local maximum point of magnetic field intensity on the X-Y plane will be moved from the farthest position from the intersection O (See FIG. 16). As shown in FIG. 18, herein, the local maximum point will be moved from a position M1 which is on the axis X, on the plus side of the intersection O and farthest from the intersection O.

Referring to FIG. 18, the circular predetermined area L has a diameter of 100 mm, and therefore the distance from the intersection O to the position M1 is 50 mm. The angle by which the permanent magnets 48a, 48b must be revolved in order for the local maximum point to make a rectilinear travel on the axis X to a target position between the intersection O and the position M1 is obtained by Mathematical Expression 1 shown below. Mathematical Expression 1 is obtained in advance experimentally, according to such factors as a magnetic characteristic of the pair of magnetic field generation units (the permanent magnets 48a, 48b in this example), the size of the gap between the two, etc. Mathematical Expression 1 is stored in memory means such as a memory chip included in an unillustrated controller.

$$D = -1.039 \times 10^{-7} r^6 + 1.381 \times 10^{-5} r^5 - 6.880 \times 10^{-4} r^4 + 1.553 \times 10^{-2} r^3 - 0.1558 r^2 - 0.6294 r + 90$$ [Mathematical Expression 1]

Mathematical Expression 1 has an item r, and by substituting it with the distance from the intersection O to the target position, an angle D by which the permanent magnets 48a, 48b must be revolved (the angle by which the rotating member 46a, 46b must be rotated) is obtained in order for the local maximum point to make a rectilinear travel on the axis X. For example, if the local maximum point is to be moved to a position M2 which is 40 mm away from the intersection O, a value 40 mm is entered to the item r in Mathematical Expression 1, and then an angle of 36.8 degrees is given as the angle D.

Therefore, by revolving the permanent magnets 49a, 48b by 36.8 degrees in mutually opposite directions, it is possible to move the local maximum point from the position M1 to the position M2. It should be noted here that the permanent magnets 48a, 48b may be revolved in whichever of the directions indicated by Arrow C1 and C2 as long as they move in mutually opposite directions (See FIG. 15). Herein, the permanent magnet 48a will be revolved in the direction indicated by Arrow C2, which then means that the permanent magnet 48b will be revolved in the direction indicated by Arrow C1.

If the target position is off the axis X, the permanent magnets 48a, 48b should be revolved while taking into account an angle made by the position M1, the intersection O and the target position (hereinafter called angle θ). For example, if the local maximum point is to be moved from the position M1 to a position M3 which is 40 mm away from the intersection O at an angle θ of 15 degrees in the direction indicated by Arrow C2 (indicated as θ1 in FIG. 18), the angle by which the permanent magnets 48a, 48b must be revolved will be obtained as follows:

Specifically, since the direction of revolution of the permanent magnet 49a is the direction indicated by Arrow C2, the angle by which the permanent magnets 48a must be revolved is obtained by adding 15 degrees to the angle D (36.8°) which can be obtained as described above, and thus an angle of 51.8 degrees is given. Also, since the direction of revolution of the permanent magnet 48b is the direction indicated by Arrow C1, the angle by which the permanent magnets 48b must be revolved is obtained by subtracting 15 degrees from the angle D (36.8°) which can be obtained as described above, and thus an angle of 21.8 degrees is given.

Therefore, by revolving the permanent magnet 48a by 51.8 degrees in the direction indicated by Arrow C2 while revolving the permanent magnet 48b by 21.8 degrees in the direction indicated by Arrow C1, it is possible to move the local maximum point from the position M1 to the position M3.

Further, if the local maximum point is to be moved from the position M3 to a position M4 which is 12.5 mm away from the intersection O at an angle θ of 190 degrees in the direction indicated by Arrow C2 (indicated as θ2 in FIG. 18), the angle by which the permanent magnets 48a, 48b must be revolved will be obtained as follows:

In this case, a value 12.5 mm is entered to the item r in Mathematical Expression 1, and then an angle of 75.1 degrees is given as the angle D. Since the direction of revolution of the permanent magnet 48a is the direction indicated by Arrow C2, addition of 190 degrees to the angle 75.1 degrees gives 265.1 degrees. Since the permanent magnet 48a was revolving by 51.8 degrees in the direction indicated by Arrow C2 when the local maximum point was moved from the position M1 to the position M3, the angle by which the permanent magnets 48a must be revolved is 213.3 degrees which is the difference obtained by subtracting 51.8 degrees from 265.1 degrees. Since the direction of revolution of the permanent magnet 48b is the direction indicated by Arrow C1, subtraction of 190 degrees from the angle 75.1 degrees gives −144.9 degrees. Since the permanent magnet 48b was revolved by 21.8 degrees in the direction indicated by Arrow C1 when the local maximum point was moved from the position M1 to the position M3, the angle by which the permanent magnet 48b must be revolved is −136.7 degrees which is the difference obtained by subtracting 21.8 degrees from −114.9 degrees. The minus (−) sign preceding the value 136.7 indicates that the direction of revolution of the permanent magnet 48b is the reverse (the direction indicated by Arrow C2 in this example).

Therefore, by revolving the permanent magnet 48a by 213.3 degrees in the direction indicated by Arrow C2 while revolving the permanent magnet 48b by 136.7 degrees in the direction indicated by Arrow C2, it is possible to move the local maximum point from the position M3 to the position M4. It should be noted here that if a target angle by which the permanent magnets 48a, 48b should be revolved exceeds 180 degrees but is smaller than 360 degrees, the permanent magnets 48a, 48b should be revolved by an angle which is equal to the difference between the target angle and 360 degrees, in the other direction than the original direction of revolution. Specifically, if the permanent magnet 48a is to be revolved by 213.3 degrees in the direction indicated by Arrow C2 as in the above example, the permanent magnet 48a should simply be revolved by 146.7 degrees in the direction indicated by Arrow C1. By revolving the permanent magnets 48a, 48b within 180 degrees angle as described above, it becomes possible to move the local maximum point efficiently.

As described, it is easy to obtain the angle by which the permanent magnets 48a, 48b must be revolved, by using a mathematical function such as Mathematical Expression 1, and it is easy to control the position of the local maximum point on the X-Y plane. The calculations as described above are performed by control means such as a CPU included in a controller.

It should be noted here that the permanent magnets used in the magnetic field generation units are not limited to the permanent magnets 16a, 16b, 48a, 48b. For example, the permanent magnets 16a, 16b may be replaced by permanent magnets 58a, 58b as shown in FIG. 19. The permanent magnets 58a, 58b include a first permanent magnet piece 60, and a pair of second permanent magnet pieces 62a, 62b opposed to each other with the first permanent magnet piece 60 in between.

The first permanent magnet piece 60 of the permanent magnet 58a is magnetized in the direction indicated by Arrow Z1. The second permanent magnet piece 62a is magnetized in the direction indicated by Arrow B1 or toward the permanent magnet piece 60. The second permanent magnet piece 62b is magnetized in the direction indicated by Arrow B2 or toward the permanent magnet piece 60. In the permanent magnet 58a, a magnetic pole (N-pole) of the first main surface 64a and a magnetic pole (S-pole) of the second main surface 66a are formed on the first permanent magnet piece 60. Also, on each of the mutually opposed surfaces (surfaces contacting the first permanent magnet piece 60) of the second permanent magnet pieces 62a, 62b, a magnetic pole of the same polarity (N-pole) as of the first main surface 64a is formed.

The permanent magnet 58b is identical with the permanent magnet 58a except that positions for the second permanent magnet pieces 62a, 62b are swapped with each other. In the permanent magnet 58b, the polarity of the first main surface 64b is S-pole. In the permanent magnet 58b, the polarity of the second main surface 66b is N-pole. Further, on each of the mutually opposed surfaces of the second permanent magnet pieces 62a, 62b in the permanent magnet 58b, the polarity of the magnetic pole is S-pole.

By using the permanent magnets 58a, 58b arranged as described as a pair of magnetic field generation units, it becomes possible to draw more magnetic flux out of the N-pole in the first main surface 64a and to gather more magnetic flux into the S-pole of the first main surface 64b. Therefore, it is possible to increase the magnetic field gradient on the predetermined plane and increase the magnetic field intensity at the local maximum point.

It should be noted here that in each of the embodiments described above, description was made for a case where the pair of magnetic field generation units are disposed in the vertical direction so one unit comes above the other. However, the present invention is not limited to this. The pair of magnetic field generation units may be disposed so the two units are placed side by side.

Also, the outer shape of the permanent magnet used in the magnetic field generation unit is not limited to the shape used in the embodiment described above, but any shape may be used.

Further, in each of the embodiments described above, description was made for a case where the pair of magnetic field generation units have the same dimensions and shape. However, the present invention is not limited to this. The pair of magnetic field generation units may have different shapes from each other. The pair of magnetic field generation units may have different sizes, too.

It should be noted here that the mode of operation for the pair of magnetic field generation units is not limited to a combination of the first operation in which the pair of magnetic field generation units are revolved relatively to each other and the second operation in which the pair of magnetic field generation units are revolved in the same direction by the same angle. It is required that at least one of the first operation and the second operation is performed whereby the local maximum point of magnetic field intensity on a predetermined plane is moved on the predetermined plane. Also, the local maximum point may be moved on the predetermined plane while the predetermined plane is moved simultaneously. Specifically, a revolving movement of the pair of magnetic field generation units and a travel of the pair of magnetic field generation units along a predetermined axis may be performed simultaneously with each other.

In each of the embodiments described above, description was made for a case where the magnetic field generation unit is provided by a permanent magnet. However, the magnetic field generation unit may use an electric magnet instead of a permanent magnet.

The present invention being thus far described and illustrated in detail, it is obvious that these description and drawings only represent examples of the present invention, and should not be interpreted as limiting the invention. The spirit and scope of the present invention is only limited by words used in the accompanied claims.

The invention claimed is:

1. A magnetic field control method of controlling a magnetic field generated by a pair of magnetic field generation units provided axially of a predetermined axis to face each other with a gap in between, each of the units having a gap-side main surface formed with a magnetic pole of an opposite polarity for each other, each magnetic pole being so disposed as to cause a magnetic flux density near the gap-side main surface to attain a local maximum off the predetermined axis, the magnetic field being controlled on a predetermined plane perpendicular to the predetermined axis and between the pair of magnetic field generation units, where the control method comprises a step of moving a local maximum point of magnetic field intensity n a predetermined plane by performing at least a first operation of revolving one of the magnetic field generation units about the predetermined axis in a direction opposite to the other of the magnetic field generation units, in the first operation and a second operation of revolving the pair of magnetic field generation units about the predetermined axis in a same direction by a same angle.

2. The magnetic field control method according to claim 1, further comprising a step of moving the predetermined plane in one direction along the axis by moving each of the magnetic field generation units in the pair in one direction by a same distance along the axis.

3. A magnetic field generator, comprising:

a pair of magnetic field generation units provided axially of a predetermined axis to face each other with a gap in between, each of the units having a gap-side main surface formed with a magnetic pole of an opposite polarity from each other, each magnetic pole being so disposed as to cause a magnetic flux density near the gap-side main surface to attain a local maximum off the predetermined axis;

first driving means for revolving one of the magnetic field generation units about the predetermined axis in a direction opposite to the other of the magnetic field generation units; and second driving means for revolving the pair of magnetic field generation units about the predetermined axis in a same direction by a same angle.

4. The magnetic field generator according to claim 3, further comprising third driving means for moving each of the magnetic field generation units in the pair in one direction along the axis by a same distance.

5. The magnetic field generator according to claim 3 or 4, wherein the magnetic field generation unit includes a permanent magnet, the magnetic pole on the gap-side main surface being formed on the permanent magnet.

6. The magnetic field generator according to claim 5, wherein the permanent magnet does not reach the predetermined axis.

7. The magnetic field generator according to claim 6, wherein the permanent magnet is formed like a segment on an annular locus.

8. A magnetic field control method of controlling a magnetic field generated by a pair of magnetic field generation units provided axially of a predetermined axis to face each other with a gap in between, each of the units having a gap-side main surface formed with a magnetic pole of an opposite polarity for each other, each magnetic pole being so disposed as to cause a magnetic flux density near the gap-side main surface to attain a local maximum off the predetermined axis, the magnetic field being controlled on a predetermined plane perpendicular to the predetermined axis and between the pair of magnetic field generation units, wherein the control method comprises a step of moving a local maximum point of magnetic field intensity on a predetermined pane by moving the local maximum point of magnetic field intensity to any position within a predetermined volume on the XYZ space by combining a first operation in which the magnetic field generation units are revolved in mutually opposite directions by the same angle and a second operation in which the magnetic field generation units are revolved in the same direction by the same angle.

9. A magnetic field generator, comprising:

a pair of magnetic field generation units provided axially of a predetermined axis to fitce each other with a gap in between, each of the units having a gap-side main surface formed with a magnetic pole of an opposite polarity from each other, each magnetic pole being so disposed as to cause a magnetic flux density near the gap-side main surface to attain a local maximum off the predetermined axis; and a driving means for moving a local maximum point of magnetic field intensity to any position within a predetermined volume on the XYZ space by combining a first operation in which the magnetic field generation units are revolved in mutually opposite directions by the same angle and a second operation in which the magnetic field generation units are revolved in the same direction by the same angle.

\* \* \* \* \*